(12) United States Patent
Takada et al.

(10) Patent No.: US 8,530,564 B2
(45) Date of Patent: Sep. 10, 2013

(54) ORGANIC-INORGANIC COMPOSITE DISPERSION, CELL CULTURE SUBSTRATE MANUFACTURED USING THE SAME, AND METHODS FOR PREPARING THE SAME

(75) Inventors: Tetsuo Takada, Chiba (JP); Kazutoshi Haraguchi, Chiba (JP)

(73) Assignees: Kawamura Institute of Chemical Research, Chiba (JP); DIC Corporation, Tokyo (JP)

( * ) Notice: Subject to any disclaimer, the term of this patent is extended or adjusted under 35 U.S.C. 154(b) by 97 days.

(21) Appl. No.: 12/997,198

(22) PCT Filed: May 25, 2009

(86) PCT No.: PCT/JP2009/059507
§ 371 (c)(1),
(2), (4) Date: Dec. 9, 2010

(87) PCT Pub. No.: WO2009/150931
PCT Pub. Date: Dec. 17, 2009

(65) Prior Publication Data
US 2011/0097802 A1    Apr. 28, 2011

(30) Foreign Application Priority Data

Jun. 12, 2008 (JP) .................. 2008-154122
Feb. 24, 2009 (JP) .................. 2009-040569

(51) Int. Cl.
*C08K 3/34* (2006.01)
*C08K 3/36* (2006.01)
*C08K 9/10* (2006.01)
*C12N 5/00* (2006.01)

(52) U.S. Cl.
USPC ........... 524/446; 524/556; 524/789; 523/204; 435/396

(58) Field of Classification Search
USPC .......... 524/446, 556, 789; 523/204; 435/396
See application file for complete search history.

(56) References Cited

U.S. PATENT DOCUMENTS

| 5,280,054 | A | * | 1/1994 | Sakai et al. | 523/521 |
| 5,856,379 | A | * | 1/1999 | Shiratsuchi et al. | 523/209 |
| 2008/0153975 | A1 | * | 6/2008 | Lubnin | 524/585 |

FOREIGN PATENT DOCUMENTS

| JP | 2-211865 A | 8/1990 |
| JP | 5-192130 A | 8/1993 |

(Continued)

OTHER PUBLICATIONS

T. J. Pinnavaia, et al., Polymer-Clay Nano Composites, Wiley, 2000.

(Continued)

*Primary Examiner* — Satya Sastri
(74) *Attorney, Agent, or Firm* — McDermott Will & Emery LLP

(57) ABSTRACT

Disclosed are: an organic-inorganic complex dispersion improved in film formability and adhesion to a base material. The organic-inorganic complex dispersion comprises an aqueous medium and particles of a complex dispersed in the aqueous medium, wherein the complex has a three-dimensional network structure formed by a polymer of a monomer comprising a monomer represented by general formula (1) and at least one inorganic material selected from a water-swellable clay mineral and silica. Also disclosed is an antifogging material manufactured by using the organic-inorganic complex dispersion. Further disclosed is a cell culture substratum improved in the detachability of cells cultured on the substratum, which is manufactured by using the organic-inorganic complex dispersion. Still further disclosed are manufacturing methods for same. [In the formula, R1 represents a hydrogen atom or a methyl group; R2 represents an alkylene group having 2 to 3 carbon atoms; R3 represents a hydrogen atom or an alkyl group having 1 to 2 carbon atoms; and n represents a number of 1 to 9].

24 Claims, 7 Drawing Sheets

(56) References Cited

FOREIGN PATENT DOCUMENTS

| | | |
|---|---|---|
| JP | 5-192138 A | 8/1993 |
| JP | 2000-212288 A | 8/2000 |
| JP | 2002-53762 A | 2/2002 |
| JP | 2004-143212 A | 5/2004 |
| JP | 2005-232402 A | 9/2005 |
| JP | 2006-169314 A | 6/2006 |
| JP | 2006-288251 A | 10/2006 |
| JP | 2008-237088 A | 10/2008 |
| WO | 02/24757 A2 | 3/2002 |
| WO | 2006/064810 A1 | 6/2006 |

OTHER PUBLICATIONS

M. Yamato, et al., Frontier of Nano-Biotechnology, Chapter 6, pp. 340-347, CMC, 2003.

* cited by examiner (a): TEM image of organic-inorganic composite particles in Example 1
(b): EDS mapping image of silicon (Si) in organic-inorganic composite particles in Example 1
(c): EDS mapping image of magnesium (Mg) in organic-inorganic composite particles in Example 1

(a): TEM image of organic-inorganic composite particles in Example 2
(b): EDS mapping image of silicon (Si) in organic-inorganic composite particles in Example 2
(c): EDS mapping image of magnesium (Mg) in organic-inorganic composite particles in Example 2

ORGANIC-INORGANIC COMPOSITE DISPERSION, CELL CULTURE SUBSTRATE MANUFACTURED USING THE SAME, AND METHODS FOR PREPARING THE SAME

CROSS REFERENCE TO PRIOR APPLICATIONS

This application is a U.S. National Phase application under 35 U.S.C. §371 of International Application No. PCT/JP2009/059507, filed on May 25, 2009 and claims benefit of priority to Japanese Patent Application No. 2008-154122, filed on Jun. 12, 2008 and Japanese Patent Application No. 2009-040569, filed on Feb. 24, 2009. The International Application was published in Japanese on Dec. 17, 2009 as WO 2009/150931A1 under PCT Article 21(2). The contents of these applications are hereby incorporated by reference.

TECHNICAL FIELD

The present invention relates to an organic-inorganic composite dispersion comprising particles of a composite dispersed in an aqueous medium, the composite comprising a polymer of a (meth)acrylic acid ester-based monomer and a water-swellable clay mineral, a cell culture substrate manufactured from the dispersion, and a preparation method thereof.

BACKGROUND ART

Polymer composites called "nano-composites" are generally prepared by compounding an organic polymer such as polyamide, polystyrene, polypropylene, polyimide or polyurethane with clay. Such polymer composites have been reported to exhibit improved properties such as elastic modulus, heat deflection temperature, gas permeability and combustion rate, due to a layer of clay having a large aspect ratio finely dispersed therein (For example, see Non-patent Document 1).

It is preferable that clay minerals are present in a great content in the polymer composites in view of performance improvement. However, it is also important to efficiently accomplish the desired properties with a lower content of clay minerals. Research to date commonly utilizes polymer composites comprising 0.2 to 5% by weight of inorganic compounds and does not utilize polymer composites comprising 0.1% by weight or less, or 10% by weight or more of inorganic compounds. This is the reason that performance improvement becomes negligible if the content of inorganic compounds used is too low, while nano-scaled fine and uniform dispersion of clay minerals in the obtained composites cannot be accomplished due to a large increase of viscosity in the preparation process, or the composites become fragile and mechanical properties (strength or elongation) thereof are thus deteriorated, if the content of inorganic compounds used is too high.

In an attempt to solve such problems, several conventional methods have been suggested. For example, as a nano-composite material with superior mechanical properties, an organic-inorganic composite hydrogel in which a clay mineral is dispersed uniformly in an organic polymer in a wide range of clay mineral content has been disclosed. It has been disclosed that, by polymerizing acrylamide or methacrylamide derivative, (meth)acrylic acid ester or others in the presence of a water-swellable clay mineral and a polymerization initiator in an aqueous medium, a polymer composite with superior mechanical properties is prepared (for examples, see Patent Documents 1 and 2).

Also, as a nanocomposite material exhibiting superior mechanical properties in a dry state, a polymer composite in which a polymer obtained from a water-soluble (meth)acrylic acid ester and a water-swellable clay mineral form a three-dimensional network has been disclosed. This polymer composite may be prepared by dissolving or uniformly dispersing a water-swellable clay mineral, a water-soluble (meth)acrylic acid ester and a polymerization initiator, and optionally a catalyst and/or an organic cross-linking agent, in water or a mixed solvent of water and an organic solvent, polymerizing the water-soluble (meth)acrylic acid ester, and drying the resulting polymer to remove the solvent (for example, see Patent Document 3).

Also, a method for rapidly preparing an organic-inorganic composite hydrogel while being not susceptible to oxygen has been disclosed. In accordance with this method, an organic-inorganic composite hydrogel with superior mechanical properties can be prepared by reacting a water-soluble acryl-based monomer in the presence of a water-swellable clay mineral by irradiating with an energy beam in a reaction solution in which a water-insoluble polymerization initiator is dispersed in an aqueous medium (for example, see Patent Document 4).

All of the aforementioned organic-inorganic composite hydrogels and polymer composites are bulk bodies and are prepared via gelling of the overall reaction system.

Meanwhile, in the field of biochemistry or medicine and industries such as the automotive industry, there is a need for organic-inorganic composite dispersions (coating materials) which exhibit superior film formability and enable formation of films exhibiting superior adhesion to substrates, or provide functionalities such as cell culture performance and antifogging properties. However, the aforementioned patent documents do not disclose an organic-inorganic composite dispersion in which organic-inorganic composite particles are dispersed in an aqueous medium, which satisfy these properties and a method for preparing the same.

Meanwhile, plastic (for example, polystyrene) vessels have been used for cell (e.g., animal tissues) culture substrates. The surface of these vessels is treated with plasma or is coated with silicon or cell adhesion agents in order to enable efficient cell culture. In the case where these cell culture vessels are used as culture substrates, the cultured (proliferated) cells are adhered to the surface of the vessels, which requires use of proteases such as trypsin or chemicals in order to detach and collect the cells. The operation for detaching the cells using enzymes or chemicals is complicated and has the risk of incorporation of various germs or impurities such as DNA or RNA. In addition, disadvantageously, regions in which cells are linked to substrates or linkages between cells are cleaved, and the cells cannot be thus collected in their proliferated forms such as sheet forms, or natures thereof are changed.

Recent research has reported use of a substrate in which a polymer (e.g., poly(N-isopropylacrylamide)) having a lower critical solution temperature is considerably thinly coated on the surface of a cell culture vessel. The polymer is hydrophobic at a cell culture temperature and cells are thus adhered to the polymer. After cell culturing, the polymer is treated at a low temperature and thus becomes hydrophilic. As a result, the adhesion between the cells and the polymer is deteriorated, and cells can thus be detached in sheet form from the substrate without using hydrolases or chemicals (for example, see Patent Documents 5 and 6, non-Patent Document 2).

However, polymers such as poly(N-isopropylacrylamide) exhibit poor adhesion to the surface of plastics such as polystyrene and applied layers thereof may be readily detached upon exposure to water. In order to prevent detachment of polymer layers from the plastic surface upon exposure to water, the polymers should be fixed to the plastic surface via a specific means. One fixing method is to apply an N-isopropylacrylamide (monomer) solution to the surface of cell culture substrates and graft-polymerize it via electron-beam irradiation (for example, see Patent Document 7).

The graft-polymerization using electron-beam irradiation necessarily entails cross-linking between polymers and great deterioration in temperature response rate of polymers with the process of cross-linking. Making the polymer hydrophilic disadvantageously involves a long low-temperature maintenance period and damage to the cells due to exposure to the low temperature for a long time. Also, cell culture substrates prepared by this method exhibit greatly deteriorated temperature response of polymers and loses cell detachability, when sterilized by radiation (for example, γ-rays).

Meanwhile, a cell culture substrate which comprises polymeric hydrogel obtained by polymerizing a water-soluble organic monomer in the presence of a water-swellable clay mineral uniformly dispersed in water by irradiation, and have a three-dimensional network structure composed of a polymer of a water-soluble organic monomer (a polymer having a lower critical solution temperature such as poly(N-isopropylacrylamide)) and a water-swellable clay mineral (for example, see Patent Document 8), are disclosed.

In biochemistry, for cell culture manipulation, there is a need for integration of a cell culture substrate with a vessel such as plastic culture dish. However, the aforementioned prior arts do not provide a specific means of integrated cell culture vessels.

In addition, a cell culture substrate using a polymer hydrogel obtained by co-polymerizing methoxyethylacrylate and N-isopropylacrylamide, in the presence of a water-swellable clay mineral uniformly dispersed in water, has been known (for example, see Patent Document 9).

However, the polymer hydrogel disclosed in this prior art is a bulk body, and is not related to an organic-inorganic composite dispersion in which particles of an organic-inorganic composite with superior film formability are dispersed in an aqueous medium. In addition, in the case where the polymer hydrogel is used as a cell culture substrate, cultured cells can be detached using a pincette, but it is not possible to collect all of the cultured cells by naturally detaching them through temperature variation.

PRIOR ART DOCUMENTS

Patent Documents

Patent Document 1: Japanese Patent Publication No. 2002-53762
Patent Document 2: Japanese Patent Publication No. 2004-143212
Patent Document 3: Japanese Patent Publication No. 2005-232402
Patent Document 4: Japanese Patent Publication No. 2006-169314
Patent Document 5: Japanese Patent Publication No. Hei 2-211865
Patent Document 6: Japanese Patent Publication No. Hei 5-192138
Patent Document 7: Japanese Patent Publication No. Hei 5-192130
Patent Document 8: Japanese Patent Publication No. 2006-288251
Patent Document 9: Japanese Patent Publication No. 2008-237088

Non-Patent Documents

Non-Patent Document 1: T. J. Pinnavaia and G. W. Beall Eds., Polymer-Clay Nano Composites, Wiley, 2000
Non-patent Document 2: Masayuki Yamato, Teruo Okano, [The forefront of Nanobiotechnology], chapter 6, P. 340-P. 347, CMC, 2003

DISCLOSURE OF THE INVENTION

Problems to be Solved by the Invention

Therefore, the present invention has been made in view of the above problems, and it is one object of the present invention to provide an aqueous dispersion, in which organic-inorganic composite particles having a three-dimensional network structure formed of a clay mineral and a polymer are stably dispersed in an aqueous medium.

It is another object of the present invention to provide an aqueous dispersion of organic-inorganic composite particles which exhibits excellent film formability and enables formation of films exhibiting superior adhesion to a substrate.

It is yet another object of the present invention to provide a cell culture substrate which solves the aforementioned problems, realizes rapid transfer between hydrophobicity and hydrophilicity in accordance with environmental temperature, does not require use of proteases such as trypsin when the cultured cells are separated and collected, and thus prevents damage to cells and readily and rapidly detaches and collects cultured cells from the surface.

Means for Solving the Problems

Patent Documents 1 to 4 relate to preparation of organic-inorganic composite hydrogels or polymer composites via gelling of the overall reaction systems. Based on the aforementioned methods, the inventors of the present invention considered a variety of methods for preparing particulate organic-inorganic composites in an aqueous medium while controlling a concentration of a clay mineral or a weight ratio of a clay mineral and an organic polymer. As a result, as shown in FIG. 1, the present inventors have discovered that, besides a region where an overall reaction system is gelled, there exists another region where a reaction system is not gelled when the contents of a monomer and a clay mineral in the reaction system are within a specific range (that is, below the limit represented by Formulae (2) and (3) in FIG. 1), thus enabling preparation of a water dispersion of organic-inorganic composite particles. Further, the present inventors have discovered that, in the region enabling preparation of a water dispersion of organic-inorganic composite particles, there exist different regions which are as follows: a region which enables preparation of organic-inorganic composite particles in which a clay mineral is uniformly dispersed in an organic polymer; and a region which enables preparation of organic-inorganic composite particles of a core-shell structure having a shell portion with a high proportion of a clay mineral and a core portion with a high proportion of an organic polymer. The present invention was accomplished based on these discoveries.

Also, as a result of extensive research into solutions to the aforementioned problems associated with cell culture substrates, the present inventors have discovered that a cell culture substrate comprising a polymer (A) of (meth)acrylic acid ester-based monomer (a), at least one inorganic material (C) selected from a water-swellable clay mineral and silica, and a polymer (B) having a lower critical solution temperature, has the ability to efficiently culture a variety of cells, the ability to readily detach the cultured cells in accordance with decrease in environmental temperature, and the ability to easily control cell culture and detachment depending on the type of cells. The present invention has been accomplished based on this discovery.

In accordance with one aspect of the present invention, provided is an organic-inorganic composite dispersion comprising particles of a composite (X) dispersed in an aqueous medium (W), the composite (X) having a three-dimensional network formed of a polymer (A) of a monomer comprising a monomer (a) represented by Formula (1) below and at least one inorganic material (C) selected from a water-swellable clay mineral and silica:

  (1)

wherein $R_1$ is a hydrogen atom or a methyl group, $R_2$ is a $C_2$-$C_3$ alkylene group, $R_3$ is a hydrogen atom or a $C_1$-$C_2$ alkyl group and n is an integer of 1 to 9.

In accordance with another aspect of the present invention, there is provided a method for preparing the organic-inorganic composite dispersion comprising: dissolving or uniformly dispersing the monomer (a), at least one inorganic material (C) selected from the water-swellable clay mineral and silica, and a polymerization initiator (D) in the aqueous medium (W) and polymerizing the monomer (a) to form the particles of the composite (X), wherein the concentration (wt %) of at least one inorganic material (C) selected from the water-swellable clay mineral and silica in the aqueous medium (W) is within the range represented by Formula (2) or (3) below:

In the case of $Ra$<0.19, the concentration (wt %) of the inorganic material $(C)$<12.4$Ra$+0.05    (2)

In the case of $Ra$≧0.19, the concentration (wt %) of the inorganic material $(C)$<0.87$Ra$+2.17    (3)

wherein the concentration (wt %) of the inorganic material (C) is a value calculated by dividing the weight of the inorganic material (C) by the total weight of the aqueous medium (W) and the inorganic material (C) and multiplying the resulting value by 100, and Ra is a weight ratio ((C)/(A)) of the inorganic material (C) to the polymer (A).

In accordance with another aspect of the present invention, there is provided a cell culture substrate comprising: a composite (X) having a three-dimensional network formed of a polymer (A) of a monomer comprising a monomer (a) represented by Formula (1) below and at least one inorganic material (C) selected from a water-swellable clay mineral and silica;

  (1)

wherein $R_1$ is a hydrogen atom or a methyl group, $R_2$ is a $C_2$-$C_3$ alkylene group, $R_3$ is a hydrogen atom or a $C_1$-$C_2$ alkyl group, and n is an integer of 1 to 9; and a polymer (B) having a lower critical solution temperature.

In accordance with another aspect of the present invention, there is provided a method for preparing the cell culture substrate comprising:

a first step of mixing the monomer (a), the inorganic material (C) and a polymerization initiator (D) in an aqueous medium (W) such that the concentration of the inorganic material (C) in the aqueous medium (W) is within the range represented by the following Formula (2) or (3), and polymerizing the monomer (a) to provide a dispersion (L) of the composite (X) comprising the polymer (A) and the inorganic material (C);

a second step of applying the dispersion (L) to a support and drying the support to form a thin layer of the composite (X);

a third step of applying a solution of a water-insoluble polymerization initiator (D) in a solvent (E) to a surface (S) of the thin layer of the composite (X) and volatilizing the solvent (E); and a fourth step of applying an aqueous solution of a monomer (b) undergoing polymerization to form the polymer (B) to the surface (S) and polymerizing the monomer (b) by UV irradiation:

In the case of $Ra$<0.19, the concentration (wt %) of the inorganic material $(C)$<12.4$Ra$+0.05    (2)

In the case of $Ra$≧0.19, the concentration (wt %) of the inorganic material $(C)$<0.87$Ra$+2.17    (3)

wherein the concentration (wt %) of the inorganic material (C) is a value calculated by dividing the weight of the inorganic material (C) by the total weight of the aqueous medium (W) and the inorganic material (C) and multiplying the resulting value by 100, and Ra is a weight ratio ((C)/(A)) of the inorganic material (C) to the polymer (A).

In accordance with another aspect of the present invention, there is provided a method for preparing the cell culture substrate comprising:

a first step of applying a mixture of the monomer (a), the inorganic material (C) and a polymerization initiator (D) in an aqueous medium (W) to a support and polymerizing the monomer (a) to form a thin layer of the composite (X) comprising the polymer (A) and the inorganic material (C);

a second step of applying a solution of a water-insoluble polymerization initiator (D) in a solvent (E) to a surface (S) of the thin layer of the composite (X) and volatilizing the solvent (E); and a third step of applying an aqueous solution of a monomer (b) undergoing polymerization to form the polymer (B) to the surface (S) and polymerizing the monomer (b) by UV irradiation.

In accordance with another aspect of the present invention, there is provided a method for preparing the cell culture substrate comprising:

a first step of mixing the monomer (a), the inorganic material (C) and a polymerization initiator (D) in an aqueous medium (W) such that the concentration of the inorganic material (C) in the aqueous medium (W) is within the range represented by the following Formula (2) or (3), and polymerizing the monomer (a) to provide a dispersion (L) of the composite (X) comprising the polymer (A) and the inorganic material (C); and a second step of adding the polymer (B) to the dispersion (L), mixing the ingredients, applying the resulting mixture to a support and drying the support:

In the case of $Ra<0.19$, the concentration (wt %) of
the inorganic material $(C)<12.4Ra+0.05$ \hfill (2)

In the case of $Ra\geqq 0.19$, the concentration (wt %) of
the inorganic material $(C)<0.87Ra+2.17$ \hfill (3)

wherein the concentration (wt %) of the inorganic material (C) is a value calculated by dividing the weight of the inorganic material (C) by the total weight of the aqueous medium (W) and the inorganic material (C) and multiplying the resulting value by 100, and Ra is a weight ratio $((C)/(A))$ of the inorganic material (C) and the polymer (A).

The cell culture substrate of the present invention is mainly characterized in that ingredients of the polymer (A) and the inorganic material (C) contribute to cell proliferation, the polymer (B) having LCST contributes to cell detachment in accordance with temperature variation and these two parts can be independently controlled, depending on the type of cells. For example, since a culture temperature (37° C.) is higher than LCST (32° C.) of poly(N-isopropylacrylamide), poly(N-isopropylacrylamide) becomes water-insoluble (hydrophobic) and cells are proliferated on the substrate surface. If temperature is downed to 32° C. or below (e.g., 20° C.), poly(N-isopropylacrylamide) becomes water-soluble (hydrophilic) and spreads from the substrate surface into the aqueous solution, and cells are thus separated and detached from the substrate.

The polymer (A) and the polymer (B) are generally linked to the inorganic material (C) via ionic or hydrogen bonds. These bonding forces are strong and the polymers are not readily separated from the inorganic material (C). For example, hydrogels (water concentration of 90%) having a three-dimensional network structure composed of poly(N-isopropylacrylamide) and a clay mineral have a tensile breaking strength of 95 kPa (See. Patent Document 8, Japanese Patent Publication 2006-288251).

The cell culture substrate of the present invention comprises a thin layer of the composite (X) in which inorganic material (C) and the polymer (A) form a substantially uniform layer structure, and a polymer (B) extending from the inside toward the surface of the thin layer.

By suitably controlling the length (molecular weight) and density (content) of the polymer (B), the surface of the thin layer of the composite (X) is not entirely covered with the polymer (B) and suitably exposed and excellent cell proliferation and cell detachment can thus be maintained.

Also, as used herein, the term "cell culture substrate" refers to a dry film of organic-inorganic composite dispersion of the present invention used for cell culture. A cell culture substrate in which the dry film is integrated with a support will be referred to as a "cell culture substrate having a laminate structure" or simply "laminate".

Effects of the Invention

The particles of the composite (X) of the present invention contain the water-swellable clay mineral with nano-level fineness and uniformity, moreover, in a wide content range, thus exhibit good stability and film formability.

Also, the film obtained from the dispersion in which the composite (X) is dispersed in a particle form, has excellent transparency, good elasticity and flexibility, and is stable in air, as well as it does not swell in water and exhibits excellent mechanical properties. In particular, the film is useful for therapeutic or cell culturing materials or antifogging materials due to superior cell culturing properties and antifogging properties thereof and is a useful surface modifier of various industrial materials and medical apparatuses due to superior transparency and elasticity.

Also, the cell culture substrate in which a polymer (B) having a lower critical solution temperature is mixed or compounded in the composite (X) exhibits rapid transition between hydrophobicity and hydrophilicity in accordance with an environmental temperature and cultured cells can be rapidly detached and collected from the substrate surface without using any agent (such as trypsin).

The cell culture substrate of the present invention exhibits superior adhesion to a substrate, thus eliminating the necessity of using a method such as electron-beam irradiation. Accordingly, the cell culture substrate avoids negative effects caused by irradiation, such as undesired cross-linkage of the polymer generated upon use of the polymer (B) having a lower critical solution temperature for the substrate, thus maintaining rapider temperature response and cell detachment and collection performance.

Also, in accordance with the preparation method of the present invention, it is possible to control the length or density of polymer (B) having a lower critical solution temperature depending on the type of cultured cells (adhesive property). The cell culture substrate of the present invention may be utilized in regenerative medicine, in manufacturing colony cell lines, 2-dimensional sheet-type cells or 3-dimensional proliferated cells.

BRIEF DESCRIPTION OF THE DRAWINGS

The above and other objects, features and other advantages of the present invention will be more transparently understood from the following detailed description taken in conjunction with the accompanying drawings, in which.

BEST MODE FOR CARRYING OUT THE INVENTION

According to the present invention, particles of a composite (X) in which at least one inorganic material (C) selected from a water-swellable clay mineral and silica are uniformly dispersed in an organic polymer (A), and particles of an organic-inorganic composite (X) of a core-shell structure having a shell portion with a high proportion of a clay mineral and a core portion with a high proportion of an organic polymer, can be prepared respectively.

Also, unlike conventional hydrogels prepared from an acrylamide-based monomer as a main ingredient, the particles of the composite (X) are not greatly water-swellable and are dispersed in an aqueous medium as water-comprising hydrogel particles. The amount of water present in the particles varies depending on the amount of monomer (a) represented by Formula (1).

Figure 1:
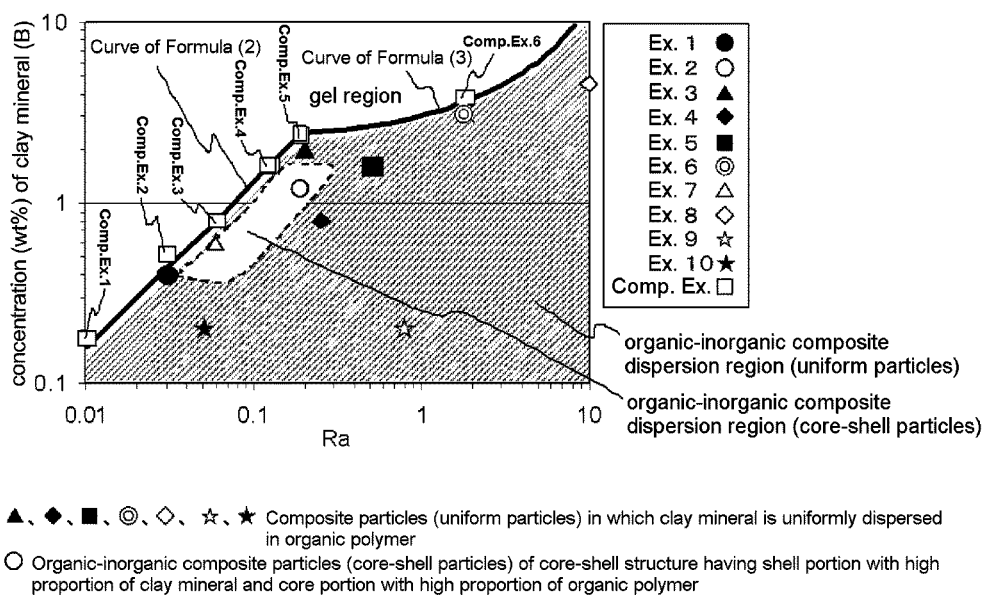
FIG. 1 shows regions in which an organic-inorganic composite dispersion satisfying Formulae (2) and (3) are formed, for Examples 1 to 7 and Comparative Example 1.
Figure 2:
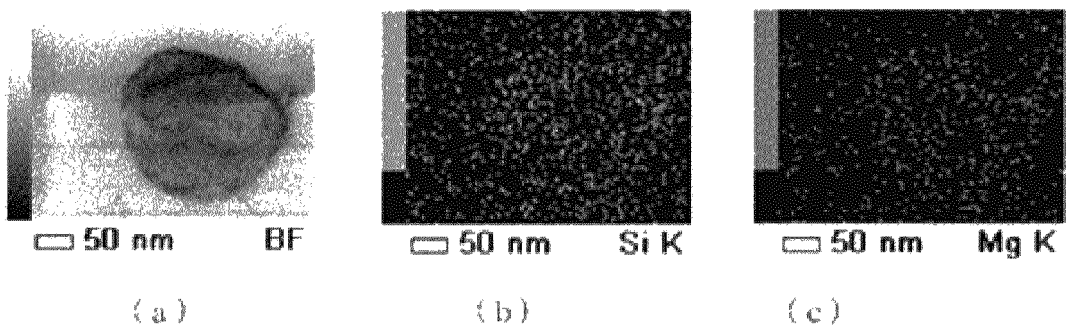
FIG. 2(a) is a TEM image of organic-inorganic composite particles in Example 1.
FIG. 2(b) is an EDS mapping image of silicon (Si) in particles of the TEM image of FIG. 2(a)
FIG. 2(c) is an EDS mapping image of magnesium (Mg) in particles of the TEM image of FIG. 2(a)

For the particles in which the organic polymer and inorganic material (C) form a three-dimensional network and are uniformly compounded, as shown in FIG. 2 (use of water-swellable clay minerals as inorganic material (C)), the dispersed state of clay minerals in the particle can be verified by TEM and element (silicon and magnesium which are main ingredients of clay minerals) mapping analysis. The particles having a uniform dispersion structure exhibit weak interaction between them and are hardly agglomerated, thus exhibit superior dispersion stability, as compared to clay minerals present alone in water. In addition, the organic polymer present on the particle surfaces is entangled each other and may form a transparent and tough film during applying and drying processes. Also, the organic polymer of the present invention exhibits excellent adhesion to substrates such as glasses, plastics or metals, thus providing strong adhesion between the films and the substrates.

Figure 3:
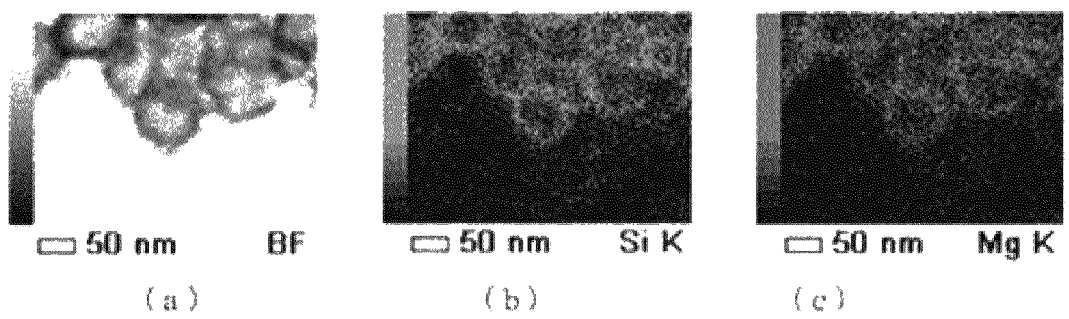
FIG. 3(a) is a TEM image of organic-inorganic composite particles in Example 2.
FIG. 3(b) is an EDS mapping image of silicon (Si) in particles of the TEM image of FIG. 3(a)
FIG. 3(c) is an EDS mapping image of magnesium (Mg) in particles of the TEM image of FIG. 3(a)

Meanwhile, as shown in FIG. 3, in the particles of a core-shell structure having a core portion which comprises the organic polymer as a main ingredient and a shell portion which comprises the clay mineral as a main ingredient, the concentration of the clay mineral is relatively high at the surface of the particles, and the film formed of the particles may thus strongly adsorb to ionic compounds, proteins or cells and the film surface can be readily functionalized.

The organic polymer (polymer (A)) used herein shows decrease of water solubility as polymerization reaction of its monomer proceeds, and is likely to be agglomerated in a sphere form when the concentration thereof gets to a certain level or higher. Accordingly, within a specific weight ratio of the inorganic material (C) and the organic polymer and a concentration of the inorganic material (C), it is considered that first the polymerization of monomers proceeds and inorganic material (C) is then agglomerated or deposited through interaction on the surface of the spherically-agglomerated organic polymer to form a core-shell structure. Meanwhile, out of the range defined above, i.e., at a low concentration of the organic polymer and/or an excessively low concentration of the inorganic material (C), the organic polymer is hardly agglomerated, and even if it is agglomerated, the amount of inorganic material (C) is insufficient to surround the organic polymer and does not form shells. Furthermore, in case that the concentration of the inorganic material (C) is excessively high, when the agglomerates comprising the organic polymer as a main ingredient are formed, inorganic material (C) is trapped in the agglomerates, therefore, the concentration difference of the inorganic material (C) between core portion and shell portion becomes not clear, and particles in which inorganic material (C) is uniformly dispersed in the organic polymer are thus formed.

The particles of the composite (X) formed in accordance with the aforementioned mechanism may have an approximately spherical shape.

The monomer (a) used herein comprises, as an essential ingredient, a monomer represented by Formula (1) below:

wherein $R_1$ is a hydrogen atom or a methyl group, $R_2$ is a $C_2$-$C_3$ alkylene group, $R_3$ is a hydrogen atom or a $C_1$-$C_2$ alkyl group and n is an integer of 1 to 9.

The use of the monomer (a) represented by Formula (1) enables easy control of particle size of the composite particles and of the composite structure of the inorganic material (C) and the polymer. In addition, the use of the monomer (a) enables preparation of organic-inorganic composites which are capable of forming smoother films due to superior properties such as dispersion stability, film formability, adhesion to substrates, and controllability of a wide range of film thickness. The monomer represented by Formula (1) may be used in a combination of two or more monomers depending on desired mechanical properties or surface properties. Preferred are monomers wherein n is an integer of 1 to 3. More preferred are 2-methoxyethyl acrylate, 2-ethoxyethyl acrylate, methylcarbitol acrylate, ethylcarbitol acrylate, methoxy triethyleneglycol acrylate, and ethoxy triethylene glycol acrylate. Most preferred are 2-methoxyethyl acrylate and 2-ethoxyethyl acrylate.

Also, other copolymerizable monomers may be used in combination with the monomer represented by Formula (1) to provide balance between hydrophilicity and hydrophobicity of organic-inorganic composites or to provide functional groups, if necessary, examples of which include acryl-based monomers having anionic groups such as sulfonyl or carboxyl groups, acryl-based monomers having cationic groups such as quaternary ammonium, acryl-based monomers having amphoteric ionic groups comprising quaternary ammonium and a phosphoric group, acryl-based monomers having amino acid residues comprising carboxyl group and amino group, acryl-based monomers comprising glucoside residues, acryl-based monomers comprising hydroxyl group, acryl-based monomers comprising polyethylene glycol or polypropylene glycol chain, amphipathic acryl-based monomers comprising hydrophilic chain such as polyethylene glycol and hydrophobic groups such as nonylphenyl group, polyethylene glycol diacrylate, N-substituted (meth)acrylamide derivatives, N,N-di-substituted (meth)acrylamide derivatives and N,N'-methylene bisacrylamide.

The inorganic material (C) used herein are at least one inorganic material selected from a water-swellable clay mineral and silica. The water-swellable clay mineral may be a swellable clay mineral which can be separated into layers, and is preferably a clay mineral capable of swelling and uniformly dispersing in water or a mixed solvent of water and an organic solvent, and is particularly preferably an inorganic clay mineral capable of uniformly dispersing in a molecular form (single layer) or level close thereto in water. More specifically, the clay mineral may contain sodium as an interlayer ion and examples thereof include water-swellable hectorite, water-swellable montmorillonite, water-swellable saponite, and water-swellable synthetic mica. These clay minerals may be used in combination.

The silica ($SiO_2$) used herein may be colloidal silica, and is preferably colloidal silica capable of uniformly dispersing in an aqueous solution and having a particle size of 10 nm to 500 nm, and preferably, of 10 to 50 nm.

The particles of the composite (X) have a structure in which the polymer (A) and the water-swellable clay mineral (B) form a three-dimensional network and are uniformly compound. This structure is preferable in that dispersion stability is excellent, tougher films can be formed, and good cell culture performance can be obtained due to strong adhesion between the film and substrates.

Alternatively, the particle of the composite (X) may have a core-shell structure comprising a core portion which comprises the polymer (A) as a main ingredient and a shell portion which comprises the inorganic material (C) as a main ingredient. This structure enables formation of films comprising a relatively high concentration of the inorganic material (C) on the surface of particles, thus providing strong adsorption to ionic compounds, proteins, peptides, heparin, antibiotics or cells, and enabling easy functionalizing of the film surface.

The aforementioned two structures of the particles of the composite (X) can be readily prepared respectively by suitably controlling the concentrations of the monomer (a) and the inorganic material (C) in the reaction solution in the preparation process.

The particles of the composite (X) preferably have a particle size of 50 nm to 5 μm, at which dispersion stability is excellent, tougher, smoother films can be formed and the thickness of films can be readily controlled.

The particles of the composite (X) of the present invention preferably have a weight ratio (i.e., (C)/(A)) of the inorganic material (C) to the polymer (A) of 0.01 to 10, and more preferably, 0.03 to 5, and particularly preferably, 0.05 to 3. The weight ratio ((C)/(A)) is preferably within the range defined above so as to achieve excellent dispersion stability, and films which are smooth and are strongly adhered to the substrates and have excellent cell culture performance.

By drying the organic-inorganic composite dispersion of the present invention, dry films which are transparent and exhibit superior flexibility and mechanical properties can be obtained. Such a film may be a film provided with the substrate or a film having no substrate. The thickness of films may be varied according to target application and is preferably 0.01 mm to 2 mm to provide easy handling. Within this range, films which are sufficiently tough and are easy to handle and have high surface smoothness can be readily prepared. Further, the thickness of the film adhered to the substrate is preferably 0.0001 mm (0.1 μm) or more, in view of considerably easy handling.

The cell culture substrates enabling superior cell adhesion or proliferation can be obtained by applying the organic-inorganic composite dispersion of the present invention to a substrate (e.g., polystyrene vessel), drying the substrate and washing the same as necessary while affixed to the substrate. The film has good adhesion to supports and is not detached in hot water or 37° C. cell culture solutions.

Also, an antifogging material to prevent formation of water drops can be prepared by adding a hydrophilic polymer (e.g., poly(N,N-dimethylacrylamide)) to the organic-inorganic composite dispersion of the present invention, applying the mixture to a substrate and drying the substrate.

Also, the organic-inorganic composite dispersion of the present invention may provide a substrate (e.g., an inner surface of artificial blood vessels or the surface of a medical apparatus embedded in the body) with cell proliferating property and improved bio-affinity, when it is applied onto the substrate, dried, washed if necessary, and then dried while affixed to the substrate.

Next, a method for preparing the organic-inorganic composite dispersion of the present invention will be described in detail.

The organic-inorganic composite dispersion of the present invention may be prepared in accordance with the following method.

The method comprises dissolving or uniformly dispersing the monomer (a), at least one inorganic material (C) selected from the water-swellable clay mineral and silica, and a polymerization initiator (D) in the aqueous medium (W) and polymerizing the monomer (a) to form the particles of the composite (X), wherein the concentration (wt %) of at least one inorganic material (C) selected from the water-swellable clay mineral and silica in the aqueous medium (W) is within the range represented by Formula (2) or (3) below:

In the case of $Ra<0.19$, the concentration (wt %) of
  the inorganic material $(C)<12.4Ra+0.05$  (2)

In the case of $Ra\geqq0.19$, the concentration (wt %) of
  the inorganic material $(C)<0.87Ra+2.17$  (3)

wherein the concentration (wt %) of the inorganic material (C) is a value calculated by dividing the weight of the inorganic material (C) by the total weight of the aqueous medium (W) and the inorganic material (C) and multiplying the resulting value by 100, and Ra is a weight ratio ((C)/(A)) of the inorganic material (C) to the polymer (A).

The monomer (a) and the inorganic material (C) used herein were defined in the illustration associated with the organic-inorganic composite dispersion and a detailed explanation thereof is thus omitted.

There are no particular limitations on the aqueous medium (W) used in the present invention provided it is able to contain a monomer (a) or an inorganic material (C) therein and allows the obtaining of organic-inorganic composite dispersions with superior physical properties. For example, the aqueous medium may include water, or aqueous solutions containing solvents miscible with water and/or other compounds. Examples of compounds contained in aqueous solutions may include preservatives, antibiotics, coloring agents, flavorings, enzymes, proteins, sugars, amino acids, cells, DNA, salts, water-soluble organic solvents, surfactants, polymer compounds, leveling agents and the like.

The polymerization initiator (D) used herein may be suitably selected from known radical polymerization initiators. Preferred is use of polymerization initiators which are dispersible in water and can be uniformly contained in the overall reaction system. Examples of polymerization initiators include water-soluble peroxides, e.g., potassium peroxodisulfate or ammonium peroxodisulfate, water-soluble azo-compounds, e.g., VA-044, V-50, V-501 (manufactured by Wako Pure Chemical Industries, Ltd.) and mixtures of $Fe^{2+}$ and hydrogen peroxide.

Suitable catalysts include N,N,N',N'-tetramethylethylenediamine as tertiary amine compound. The catalysts are not necessarily used. The polymerization temperature is determined according the types of polymerization catalysts or initiators and is preferably 0° C. to 100° C. The polymerization period may be within the range of several tens seconds to several tens hours.

Meanwhile, the photopolymerization initiator is suitably used, since it is not susceptible to oxygen inhibition and exhibits high polymerization rate. Examples of suitable photopolymerization initiators include acetophenones such as p-tert-butyl trichloroacetophenone, benzophenones such as 4,4'-bisdimethylaminobenzophenone, ketones such as 2-methylthioxanthone, benzoin ethers such as benzoin methyl ether, α-hydroxyketones such as hydroxycyclohexyl phenyl ketone, phenyl glyoxylates such as methyl benzoyl formate and metallocenes.

The photopolymerization initiator is water-insoluble. The term "water-insoluble" as used herein refers to a property in which a polymerization initiator is dissolved in an amount of 0.5% by weight or less in water. Preferred is use of the water-insoluble polymerization initiator in that the initiator can be present closer to the inorganic material (C), initiation reaction points which are present adjacent to the inorganic material (C) increase, thus the obtained organic-inorganic composite has a narrow particle size distribution and superior dispersion stability.

Preferably, a solution of the photopolymerization initiator in a solvent (E) which is compatible to the aqueous medium (W) may be added to the aqueous medium (W). This method enables more uniform dispersion of the photopolymerization initiator, thus obtaining particles of the composite (X) having a more uniform particle size.

The solvent (E) used herein may be a water-soluble solvent capable of dissolving the photo-polymerization initiator (D) or the water-insoluble polymerization initiator (D); or, a monomer (a) represented by Formula (1) or another acryl-based monomer (a'), capable of dissolving the photopolymerization initiator (D) and the water-insoluble polymerization initiator (D) and has a hydrophilic-hydrophobic balance (HLB) value of 8 or higher. The HLB value is calculated using Davis's Equation ([Surfactants-properties, applications and chemoecology], Ayao Kitahara et al., Kodansha, 1979, p. 24-27). Examples of suitable solvents include polypropylene glycol diacrylates such as tripropylene glycol diacrylate; polyethylene glycol diacrylates; polypropylene glycol acrylates such as pentapropylene glycol acrylate; polyethylene glycol acrylates; methoxy polyethylene glycol acrylates such as methoxyethyl acrylate, methoxy triethylene glycol acrylate; nonylphenoxy polyethylene glycol acrylates; N-substituted acrylamides such as dimethyl acrylamide; hydroxyethyl acrylates; hydroxypropyl acrylates; and the like. The acryl-based monomer having a HLB value of 8 or higher is preferable as the solvent (E) due to superior solubility or dispersibility in the aqueous medium (W). These acryl-based monomers may be used in combination of one or more monomers.

The term "water-soluble solvent" as used herein refers to a solvent of which 50 g or more is able to be dissolved in 100 g of water. Within this range, dispersibility of water-insoluble photopolymerization initiator (D) in an aqueous medium (W) is superior, the particle size of the composite (X) thus obtained can be readily uniformized and dispersion stability is thus excellent.

For the solution of the water-insoluble photopolymerization initiator (D) in the solvent (E), the weight ratio (D)/(E) of the photopolymerization initiator (D) to the solvent (E) is preferably 0.001 to 0.1, and more preferably 0.01 to 0.05. When the weight ratio is 0.001 or higher, the amount of radicals generated by energy beam irradiation is sufficient, thus contributing to smooth polymerization. When the weight ratio is 0.1 or lower, colors or odors are not generated substantially from the initiator, thus cost is saved.

For both the acryl-based monomer (a') and the water-soluble solvent, the amount of the solution of the photopolymerization initiator (D) in the solvent (E) is preferably 0.1% to 5% by weight with respect to the total weight of the monomer (a), the inorganic material (C), the aqueous medium (W), the polymerization initiator (D) and the solvent (E), more preferably, 0.2% to 2% by weight. When the dispersed amount is 0.1% by weight or more, initiation of polymerization is sufficient, and when the dispersed amount is 5% by weight or less, problems such as odor caused by increase of polymerization initiator in the particles of the composite (X) and re-agglomeration of dispersed photopolymerization initiator are reduced and a uniform organic-inorganic composite dispersion can thus be obtained.

In the preparation of the organic-inorganic composite dispersion according to the present invention, the most important feature is that the concentration (wt %) of the inorganic material (C) in the aqueous medium is within the range represented by Formula (2) or (3). When the concentration (wt %) of the inorganic material (C) in the aqueous medium is the defined level or higher, the overall reaction system may be gelled by polymerization or the dispersion (L) may be heterogeneous, thus making it impossible to prepare a suitable organic-inorganic composite dispersion.

The particles of the composite (X) in which the polymer (A) and the inorganic material (C) form a three-dimensional network and are uniformly compounded, and the particles of the composite (X) having a core-shell structure comprising a core portion which comprises the polymer (A) as a main ingredient and a shell portion which comprises the inorganic material (C) as a main ingredient can be readily prepared respectively by suitably controlling the concentration of the inorganic material (C) and the monomer (a) in the aqueous medium (W). For example, when the concentration of the inorganic material (C) in the aqueous medium (W) exceeds 1.2% by weight, or when the concentration of the monomer (a) is less than 6.0% by weight, particles of the composite (X) having a uniform composite structure are obtained. On the other hand, when the concentration of the inorganic material (C) in the aqueous medium (W) is 1.2% by weight or lower and the concentration of the monomer (a) is 6.0% by weight or higher, particles of composite (X) having a core-shell composite structure can be obtained.

The organic-inorganic composite dispersions prepared by the method according to the present invention may be used as coating materials directly, or after further purification through washing. Also, to provide the dispersion with applicability, or to provide the dry film made from the dispersion with functionalities such as surface smoothness, cell culturing/detachability and antifogging, additives such as leveling agents, surfactants, polymer compounds, peptides, proteins and collagen may be added to the organic-inorganic composite dispersion.

Also, by applying the organic-inorganic composite dispersion of the present invention to a support and drying to form a dry film, a laminate can be produced. It is preferable that the dispersion be applied in a predetermined pattern on the support in order to realize superior cell culture effects and to facilitate cell detachment/collection. Methods for applying organic-inorganic composite dispersions in a predetermined pattern on the support include: a printing, comprising applying the dispersion to a patterned plate and transcribing it to a support; a patterned applying, comprising shielding a region that is not to be applied, applying the dispersion, and removing the shielding; and an inkjet printing.

There are no particular limitations on the pattern applied used in the present invention provided it has repeating period of $10^{-3}$ to $10^1$ mm. Preferable patterns include line, lattice, and dot patterns and vortex, concentric circle or fractal patterns, having repeating period of $10^{-3}$ to $10^1$ mm.

By applying the dispersion to a support in which cells are not adhered or proliferated (e.g., polystyrene not subjected to corona discharge), superior effect such as good cell culturing, detaching and collecting of the cells or cell thin films using little or no enzymatic treatment, and superior spheroid formation and collecting, can be obtained. In examples using Balb3T3 cells (established mouse fibroblast cell line) or normal human dermal fibroblast cells, the organic-inorganic composite dispersion is applied in a pattern having predetermined repeating period. If the gap between the applied regions is sufficiently narrow, the cells are proliferated over the unapplied regions, and are thus finally proliferated throughout the overall support surface. Moreover, areas at which the cultured cell layer is adhered to the support are small, and cell culture substrates enabling easy cell detachment can thus be obtained. The gap between regions to which the dispersion is applied (the width of unapplied region) is preferably 300 µm or less, more preferably, 200 µm or less, most preferably, 100 µm or less. When the gap is 300 µm or less, cells are proliferated over the width of unapplied region, thus obtaining good cell layers.

The polymerization using the photopolymerization initiator may be carried out by energy-beam irradiation and electron-beam, γ-rays, X-rays, ultraviolet rays and visible light may be used. Of these, ultraviolet rays is preferred in light of apparatus simplicity and handling convenience. The irradiation intensity of ultraviolet rays is preferably 10 to 500 mW/cm$^2$ and an irradiation period is generally 0.1 to 200 seconds. Although oxygen acts as an inhibitor of polymerization in general radical polymerization using heating, the present invention eliminates the necessity of shielding oxygen in the solution preparation and polymerization via energy-beam irradiation, and may perform these processes under an air atmosphere. In some cases, the polymerization rate can be further accelerated by performing UV irradiation under an inert gas atmosphere.

The polymerization of dispersion (L) comprising the monomer (a), the inorganic material (C), the water-insoluble polymerization initiator (D) and the aqueous medium (W) using energy-beam irradiation may be selected from well-known methods such as discontinuous preparation methods using polymerization by energy beam irradiation while stirring and/or subjecting ultrasonic vibration to the dispersion (L) in a vessel, or continuous preparation methods using polymerization by energy beam irradiation while flowing the dispersion (L) through a transparent pipe (including micro channels).

<Cell Culture Substrates Comprising Polymer (B) having Lower Critical Solution Temperature>

Hereinafter, cell culture substrates comprising the polymer (B) having a lower critical solution temperature and a method for preparing the same will be illustrated in detail.

The monomer (a) used for the preparation of the cell culture substrates comprising the polymer (B) comprises the monomer of Formula (1) as an essential ingredient. By using the monomer represented by Formula (1), initial adhesion of cells can be readily controlled and cell culture substrates with superior cell proliferation and detachability can thus be obtained. Also, when the cell culture substrates are laminated on the surface of a support composed of a plastic material such as polystyrene, adhesion there between is strong and easy preparation is thus realized.

The monomer represented by Formula (1) may be used in a combination of one or more monomers depending on required mechanical properties or surface properties. Also, under the conditions that culture properties or physical properties of the cell culture substrates are not affected, as other co-monomers, monomers used for the preparation of the particles of the composite (X) may be used, if necessary.

The compounds used for the preparation of the particles of the composite (X) may also be used as a inorganic material (C) for preparation of cell culture substrates of the present invention.

For the cell culture substrates, the weight ratio ((C)/(A)) of the inorganic material (C) to the polymer (A) is preferably 0.01 to 10 and more preferably 0.03 to 5. The weight ratio ((C)/(A)) within the range defined above is preferable, in that the composite structure of the clay mineral or silica and the polymer (A) (for example, core-shell structure comprising a shell (outer) portion which comprises the clay mineral as a main ingredient and a core (inner) portion which comprises the polymer (A) as a main ingredient, or a uniform structure in which the clay mineral and polymer (A) are uniformly compounded, etc) can be easily designed, and applied (coated) films with superior surface properties (e.g., hydrophilicity or hydrophobicity, or cell culture performance) and physical properties, high uniformity, good adhesion to support and non-brittleness can thus be obtained.

For the cell culture substrates, the content of the polymer (B) with respect to the total weight of the culture substrate is preferably 0.0001% to 40% by weight, more preferably, 0.01 to 30% by weight, particularly preferably, 1 to 20% by weight.

When the content of the polymer (B) is 0.0001% to 40% by weight, the culture substrates exhibit improved cell adhesion and proliferation and detachability upon decrease in temperature, excellent surface smoothness, and superior applicability or adhesion to substrate surfaces when laminated on the surface of plastic substrates.

For the polymer (B) having a lower critical solution temperature (hereinafter, referred to simply as "LCST"), any polymer may be suitably used without particular limitation provided the molecular structure of the polymer has a moiety expressing LOST behavior. The polymer may be based upon at least one monomer (b) selected from the group consisting of N-substituted (meth)acrylamide derivatives and N,N-disubstituted (meth)acrylamide derivatives. Examples of useful monomers (b) include N-isopropyl(meth)acrylamide, N-n-propyl(meth)acrylamide, N-cyclopropyl(meth)acrylamide, N-ethoxyethyl(meth)acrylamide, N-tetrahydrofurfuryl (meth)acrylamide, N-ethyl(meth)acrylamide, N-ethyl-N-methyl(meth)acrylamide, N,N-diethyl(meth)acrylamide, N-methyl-N-n-propyl(meth)acrylamide, N-methyl-N-isopropyl(meth)acrylamide, N-(meth)acryloyl piperidine, N-(meth)acryloyl pyrolidine.

The monomers may be used alone or in combination, as necessary. Also, any copolymers of the monomer (b) with other water-soluble organic monomers or organic solvent-soluble organic monomers may be used so long as polymers obtained are both hydrophilic and hydrophobic.

As herein used, the term "lower critical solution temperature (LOST)" refers to a critical temperature at or above which a polymer is not dissolved in water (becomes hydrophobic), while the polymer is dissolved in water (becomes hydrophilic) below the temperature. For example, LOST of poly(N-isopropylacrylamide) is 32° C.

Next, a method for preparing the cell culture substrates of the present invention will be illustrated in detail.

Following three methods are provided.

A first method is a method for preparing the cell culture substrates, comprising:

a first step of mixing the monomer (a), the inorganic material (C) and a polymerization initiator (D) in an aqueous medium (W) such that the concentration of the inorganic material (C) in the aqueous medium (W) is within the range represented by the following Formula (2) or (3), and polymerizing the monomer (a) to provide a dispersion (L) of the composite (X) comprising the polymer (A) and the inorganic material (C);

a second step of applying the dispersion (L) to a support and drying the support to form a thin layer of the composite (X);

a third step of applying a solution of a water-insoluble polymerization initiator (D) in a solvent (E) to a surface (S) of the thin layer of the composite (X) and volatilizing the solvent (E); and a fourth step of applying an aqueous solution of a monomer (b) undergoing polymerization to form the polymer (B) to the surface (S) and polymerizing the monomer (b) by UV irradiation:

In the case of $Ra<0.19$, the concentration (wt %) of
the inorganic material $(C)<12.4Ra+0.05$ (2)

In the case of $Ra\geq 0.19$, the concentration (wt %) of
the inorganic material $(C)<0.87Ra+2.17$ (3)

wherein the concentration (wt %) of the inorganic material (C) is a value calculated by dividing the weight of the inorganic material (C) by the total weight of the aqueous medium (W) and the inorganic material (C) and multiplying the resulting value by 100, and Ra is a weight ratio $((C)/(A))$ of the inorganic material (C) to the polymer (A).

The monomer (a), the inorganic material (C) and the monomer (b) herein used may be the same as in the illustration of the cell culture substrates and a detailed explanation thereof will be omitted.

There are no particular limitations on the aqueous medium (W) used in the present invention provided it is able to contain the monomer (a), inorganic material (C) and the like and organic-inorganic composite dispersions with superior physical properties can be obtained by polymerization. Examples of suitable aqueous media include water, aqueous solutions comprising solvents miscible with water and/or other compounds. Examples of compounds contained in aqueous solutions may include preservatives, antibiotics, coloring agents, flavorings, enzymes, proteins, collagen, sugars, amino acids, cells, DNA, salts, water-soluble organic solvents, surfactants, polymer compounds, leveling agents and the like.

The polymerization initiator (D) used herein may be suitably selected from aforementioned known radical polymerization initiators.

Suitable catalysts include N,N,N',N'-tetramethylethylenediamine as tertiary amine compound. The catalysts are not necessarily used. The polymerization temperature is determined according the types of polymerization catalysts or initiators and is preferably 0° C. to 100° C. The polymerization period may be within the range of several tens seconds to several tens hours.

Meanwhile, the photopolymerization initiator is suitably used as the polymerization inhibitor (D), since it is not susceptible to oxygen inhibition and exhibits high polymerization rate. Specifically, the aforementioned photopolymerization initiator may be used.

For the solution of the photopolymerization initiator (D) in a solvent (E), the weight ratio (D)/(E) of the photopolymerization initiator (D) to the solvent (E) is preferably 0.001 to 0.1, and more preferably 0.01 to 0.05. When the weight ratio is 0.001 or higher, the amount of radicals generated by ultraviolet irradiation is sufficient, thus contributing to smooth polymerization. When the weight ratio is 0.1 or less, there is substantially no occurrence of colors or odors caused by the initiator, thus cost is saved.

The amount of the solution of photo-polymerization initiator (D) in the solvent (E) is preferably 0.1% to 5% by weight with respect to the total weight of the monomer (a), the inorganic material (C), the aqueous medium (W), the polymerization initiator (D) and the solvent (E), more preferably, 0.2% to 2% by weight. When the dispersed amount is 0.1% by weight or more, initiation of polymerization is sufficient, and when the dispersed amount is less than 5% by weight, problems such as odor caused by increase of the polymerization initiator in the composite (X) and re-agglomeration of dispersed photopolymerization initiator are reduced and uniform dispersion (L) of the composite (X) can thus be obtained.

In the fourth step, the use water-insoluble polymerization initiator (D) is preferred, in that, when the aqueous solution of the monomer (b) is applied, the initiator is not eluted, more initiation reaction points are present adjacent to clay mineral or silica, and interaction between the obtained polymer (B) and inorganic material (C) is thus stronger.

The most critical feature of the preparation of the cell culture substrate according to the present invention is that the concentration (wt %) of the inorganic material (C) in the aqueous medium is within the range represented by Formula (2) or (3). When the concentration (wt %) of the inorganic material (C) in the aqueous medium is within the range defined above, good dispersion (L) of the composite (X) is obtained, which is readily applied to a support, and thereby thin applied (coated) film which is smooth is obtained The dispersion (L) prepared by the method according to the present invention may be used directly or after further purification by washing. Also, additives such as leveling agents, surfactants, peptides, proteins, collagen, amino acids, and polymer compounds may be added to the dispersion.

In the second step of this method, application of the dispersion (L) to the support may be carried out in accordance with a well-known manner. Examples of application methods include casting the dispersion to a support; applying using a bar coater or spin coater; spraying; applying a dispersion to a patterned rubber substrate and transcribing it to a support; patterned applying comprising shielding a region that is not to be applied, applying the dispersion, and removing the shielded region; and inkjet printing.

By applying the dispersion (L) in a pattern to a support in which cells are not adhered or proliferated (e.g., polystyrene not subjected to corona discharge), when the gap between applied regions is sufficiently narrow, the cells are proliferated over the unapplied regions, and are thus finally proliferated throughout the overall support surface, and furthermore, areas at which the cultured cell layer is adhered to the support are small and cell culture substrates enabling easy cell detachment can thus be obtained. The gap between boundaries of applied regions (the width of unapplied region) is 300 μm or less, more preferably, 200 μm or less, most preferably, 100 μm or less. When the gap is 300 μm or less, cells are sufficiently proliferated over the width of unapplied regions, thus obtaining good cell layers.

Any drying method may be used so long as volatile ingredients in the dispersion (L) are volatilized and a thin layer of the composite (X) can be formed. Examples of suitable drying methods include natural drying at room temperature, air drying at room temperature, heating, or hot-air drying, far-infrared radiation drying and the like. Another drying method is to heat the dispersion, or to expose the dispersion to hot air while spin-coating the dispersion.

In the third step, application of the solution of the water-insoluble polymerization initiator (D) in the solvent (E) to the surface (S) of the thin layer of the composite (X) or volatizing the solvent (E) may be carried out by a well-known method as illustrated in the second step.

The solution (D+E) applied to the surface (S) is permeated into the thin layer of the composite (X), the solvent (E) is volatilized and the initiator is thus uniformly present throughout the overall thin layer of the composite (X). The aforementioned photopolymerization initiators may be used as the water-insoluble polymerization initiator (D). In the fourth step, the use of the water-insoluble polymerization initiator (D) is preferred, in that, when the monomer (b) aqueous solution is applied, the elution of the initiator is little, more initiation reaction points are present adjacent to clay mineral or silica, and interaction between the obtained polymer (B) and inorganic material (C) is thus stronger.

For the solution of the water-insoluble polymerization initiator (D) in a solvent (E), the weight ratio (D)/(E) of the polymerization initiator (D) and the solvent (E) is preferably 0.001 to 0.1, and more preferably 0.01 to 0.05. When the weight ratio is 0.001 or higher, the amount of radicals generated by ultraviolet irradiation is sufficient, thus contributing to smooth polymerization. When the weight ratio is 0.1 or less, colors or odors caused by the initiator are not generated substantially, thus cost is saved.

The aforementioned solvent (E) may be used as the solvent (E) in this method. The acryl-based monomer having a HLB value of 8 or higher used as the solvent (E) is preferable due to superior solubility or dispensability in an aqueous medium (W).

In the fourth step, application of the aqueous solution of the monomer (b) to the surface (S) may be carried out by well-known methods as illustrated in the second step.

The concentration of the monomer (b) in its aqueous solution is preferably 1 to 20% by weight, more preferably, 5 to 18% by weight. When the concentration is 1% by weight or higher, the polymer (B) having a sufficient length is obtained and cell detachability can thus be maintained, and when the concentration is 20% by weight or lower, sufficient cell proliferation can be maintained and cell culture substrates with superior performance can be prepared.

The monomer (b) applied to the surface (S) is permeated into the thin layer of the composite (X) and is polymerized via UV irradiation. The surface of the cell culture substrate obtained by this method is not entirely covered with the layer composed of the polymer (polymer (B)) of the monomer (b), but the polymer (B) is extending from inside the thin layer of the composite (X) and the surface of the thin layer is also suitably exposed. The polymer (B) is bound to the clay mineral from the inside to the surface of the thin layer of the composite (X) via ionic bonds or hydrogen bonds and the bonds are not cleaved and are stable upon application of physical force or in the presence of water. Also, depending on the type of cultured cells, the length (molecular weight) or density (the content in thin layer of composite (X)) of the polymer (B) can be suitably controlled by the concentration or applying amount of aqueous solution of the monomer (b).

Examples of radiation that can be used for the process include electron-beam, γ-rays, X-rays, ultraviolet rays and visible light. Of these, ultraviolet rays is preferred in light of apparatus simplicity and handling convenience and as it does not cause cross-linking upon polymerization of the monomer (b). The intensity of ultraviolet rays irradiated is preferably 10 to 500 mW/cm$^2$ and the irradiation period is generally 0.1 to 200 seconds. Although oxygen acts as an inhibitor of polymerization in general radical polymerization using heating, the present invention eliminates the necessity of performing solution preparation and polymerization via ultraviolet irradiation under an oxygen-free atmosphere and may perform these processes under an air atmosphere. In some cases, the polymerization rate can be further accelerated by performing UV irradiation under an inert gas atmosphere.

The first preparation method is characterized in that proliferation of cells can be greatly controlled by adjusting a ratio of the monomer (a) and the inorganic material (C), and detachment rate of cells in accordance with variations in temperature can be controlled by adjusting the type, concentration and applying amount of the monomer (b).

A second preparation method for preparing a cell culture substrate comprising:

a first step of applying a mixture of the monomer (a), the inorganic material (C) and a polymerization initiator (D) in an aqueous medium (W) to a support and polymerizing the monomer (a) to form a thin layer of the composite (X) comprising the polymer (A) and the inorganic material (C);

a second step of applying a solution of a water-insoluble polymerization initiator (D) in a solvent (E) to a surface (S) of the thin layer of the composite (X) and volatilizing the solvent (E); and a third step of applying an aqueous solution of a monomer (b) undergoing polymerization to form the polymer (B) to the surface (S) and polymerizing the monomer (b) by UV irradiation.

The application method, ultraviolet rays, concentration of the polymerization initiator (D) and monomer (b) of the second method are defined as in the first method. In the first step of this method, a thin layer of the composite (X) is directly prepared from a reaction solution, thus eliminating the necessity of adjusting the concentration of the inorganic material (C) in the aqueous medium (W) within the range defined by Formula (2) or (3). The surface structure of the cell culture substrate prepared by this method is substantially identical to that obtained with the first method.

A third preparation method for preparing a cell culture substrate comprising:

a first step of mixing the monomer (a), the inorganic material (C) and a polymerization initiator (D) in an aqueous medium (W) such that the concentration of the inorganic material (C) in the aqueous medium (W) is within the range represented by the following Formula (2) or (3), and polymerizing the monomer (a) to provide a dispersion (L) of the composite (X) comprising the polymer (A) and the inorganic material (C); and a second step of adding the polymer (B) to the dispersion (L), mixing the ingredients, applying the resulting mixture to a support and drying the support:

$$\text{In the case of } Ra<0.19, \text{ the concentration (wt \%) of the inorganic material } (C)<12.4Ra+0.05 \qquad (2)$$

$$\text{In the case of } Ra\geq 0.19, \text{ the concentration (wt \%) of the inorganic material } (C)<0.87Ra+2.17 \qquad (3)$$

wherein the concentration (wt %) of the inorganic material (C) is a value calculated by dividing the weight of the inorganic material (C) by the total weight of the aqueous medium (W) and the inorganic material (C) and multiplying the resulting value by 100, and Ra is a weight ratio ((C)/(A)) of the inorganic material (C) to the polymer (A).

A 10 wt % aqueous solution of the polymer (B) used for this method preferably has a viscosity of 20 to 2,000 mPa·s (measured with DIGITAL VISCOMATE MODEL VM-100A viscometer available from Yamaichi Denki Co., Ltd.), more preferably 100 to 1,000 mPa·s and most preferably, 200 to 800 mPa·s. When the viscosity is 20 mPa·s or higher, sufficient cell detachability can be maintained, and when the viscosity is 1,000 mPa·s or less, sufficient cell proliferation can be maintained and cell culture substrates with superior properties can thus be obtained.

Also, the polymer (B) used for the method preferably has a weight average molecular weight (Mw) of $1\times10^4$ to $2\times10^7$, more preferably, $1\times10^5$ to $5\times10^5$. When the Mw is $1\times10^4$ or higher, sufficient cell detachability can be maintained, and when the Mw is $2\times10^7$ or lower, sufficient cell proliferation can be maintained and cell culture substrates with superior properties can thus be obtained.

The surface of cell culture substrates obtained by this method is not entirely covered with the layer formed of the polymer (B). The polymer (B) is extending from the inside the thin layer of the composite (X) and the surface of the thin layer is also suitably exposed. The polymer (B) is bound to the clay mineral or silica from the inside to the surface of the thin layer of the composite (X) via ionic bonds or hydrogen bonds and these bonds are thus not cleaved and are stable upon application of physical force or in the presence of water. Also, the length (molecular weight) or the concentration of the polymer (B) can be suitably controlled in consideration of the type of cells to be cultured.

EXAMPLES

Now, the present invention will be described in more detail with reference to the following Examples. These examples should not be construed as limiting the scope and spirit of the present invention.

Example 1

Preparation of Solution (G) of Photopolymerization Initiator (D) in Solvent (E)

9.8 g of ethanol as a solvent (E) and 0.2 g of 1-hydroxycyclohexyl phenyl ketone "Irgacure 184" (Ciba-Geigy Ltd.) as a water-insoluble photopolymerization initiator (D) were uniformly mixed to prepare a solution (G1).
[Preparation of Reaction Solution (F) Comprising Monomer (a), Water-Swellable Clay Mineral (B), Water-Insoluble Photopolymerization Initiator (D) and Aqueous Medium (W)]

1.3 g of 2-methoxyethyl acrylate (available from Toagosei Co., Ltd.) as a monomer (a), 0.04 g of Laponite XLG (water-swellable synthetic hectorite available from Rockwood Additives Ltd.) as a clay mineral (B), 25 μL of the solution (G1) as a water-insoluble photopolymerization initiator (D) and 10 g of water as an aqueous medium (W) were uniformly mixed to prepare a reaction solution (F1).
[Preparation of Organic-Inorganic Composite Dispersion]

The reaction solution (F1) was irradiated with ultraviolet rays (with intensity 40 mW/cm$^2$ at 365 nm) for 180 seconds while being stirred with a magnetic stirrer to prepare a white organic-inorganic composite dispersion (MNC0.5M1).

The particle size distribution of the organic-inorganic composite dispersion (MNC0.5M1) was measured using a particle size distribution measurement apparatus (Microtrac UPA 150 available from Nikkiso Co., Ltd.) and an average particle size thus obtained was 180 nm.

The organic-inorganic composite dispersion (MNC0.5M1) was 10-fold diluted with pure water, was mixed with a same amount of 0.5 wt % RuO$_4$ aqueous solution and thereby composite particles were stained. Subsequently, the resulting aqueous solution was added dropwise to a copper net provided with a supporting film, dried and subjected to TEM-EDS mapping (analysis for distribution of clay mineral in particles of composite (X)) with a transmission electron microscope (JEM-2200 FS available from JEOL Ltd., acceleration voltage of 200 KV). The mapping measurement results confirmed that the clay mineral was uniformly dispersed in the particle. The TEM and EDS mapping images are shown in FIG. 2. FIG. 2(a) is a TEM image of organic-inorganic composite particles, FIG. 2(b) is an EDS mapping image of silicon (Si) in particles of the TEM image of FIG. 2(a), and FIG. 2(c) is an EDS mapping image of magnesium (Mg) in particles of the TEM image of FIG. 2(a). FIGS. 2(b) and 2(c) are images having the same sight and magnification as FIG. 2(a). Also, formation processes of samples for TEM-EDS measurement inevitably allow clay mineral, dispersed in the aqueous medium, to be left in the background after drying, and thus showing presence of Si and Mg in regions other than the particles.

The organic-inorganic composite dispersion (MNC0.5M1) was placed in a glass screw tube, and then allowed to stand in a hermetically sealed state at ambient temperature (about 23° C.) for 3 months. As a result, neither precipitation nor variation in particle size distribution was observed.

In this reaction system, Ra was 0.03 and the concentration (wt %) of the clay mineral (B) was 0.40(%)<12.4Ra+0.05=0.42.

Example 2

Preparation of Reaction Solution (F) Comprising Monomer (a), Water-Swellable Clay Mineral (B), Water-Insoluble Photopolymerization Initiator (D) and Aqueous Medium (W)

0.64 g of 2-methoxyethyl acrylate (available from Toagosei Co., Ltd.) as a monomer (a), 0.12 g of Laponite XLG (available from Rockwood Additives Ltd.) as a clay mineral (B), 25 μl of the solution (G1) as a water-insoluble photopolymerization initiator (D) and 10 g of water as an aqueous medium (W) were uniformly mixed to prepare a reaction solution (F2).
[Preparation of Organic-Inorganic Composite Dispersion]

The reaction solution (F2) was irradiated with ultraviolet rays (with intensity 40 mW/cm$^2$ at 365 nm) for 180 seconds while being stirred with a magnetic stirrer to prepare a slightly milky white organic-inorganic composite dispersion (MNC1.5M0.5).

The particle size distribution of the organic-inorganic composite dispersion (MNC1.5M0.5) was measured using a particle size distribution measurement apparatus (Microtrac UPA 150 available from Nikkiso Co., Ltd.) and an average particle size thus obtained was 70 nm.

The organic-inorganic composite dispersion (MNC1.5M0.5) was pre-treated, dried, and subjected to TEM-EDS mapping measurement with a transmission electron microscope in the same manner as in Example 1. The results of the mapping measurement showed core-shell structure in which clay mineral was localized at the surface portion of the particle. A TEM image and an EDS mapping image of the composite particles are shown in FIG. 3. FIG. 3(a) is a TEM image of organic-inorganic composite particles, FIG. 3(b) is an EDS mapping image of silicon (Si) in particles of the TEM image of FIG. 3(a), and FIG. 3(c) is an EDS mapping image of magnesium (Mg) in particles of the TEM image of FIG. 3(a).

In this reaction system, Ra was 0.19 and the concentration (wt %) of the clay mineral (B) was 1.19(%)<0.87Ra+2.17=2.34.

Example 3

Preparation of Reaction Solution (F) Comprising Monomer (a), Water-Swellable Clay Mineral (B), Water-Insoluble Photopolymerization Initiator (D) and Aqueous Medium (W)

1.0 g of 2-methoxyethyl acrylate (available from Toagosei Co., Ltd.) as a monomer (a), 0.2 g of Laponite XLG (available from Rockwood Additives Ltd.) as a clay mineral (B), 25 µl of the solution (G1) as a water-insoluble photopolymerization initiator (D) and 10 g of water as an aqueous medium (W) were uniformly mixed to prepare a reaction solution (F3).

[Preparation of Organic-Inorganic Composite Dispersion]

The reaction solution (F3) was irradiated with ultraviolet rays (with intensity 40 mW/cm$^2$ at 365 nm) for 180 seconds while being stirred with a magnetic stirrer to prepare a slightly milky white organic-inorganic composite dispersion (MNC2.5M0.8).

The particle size distribution of the organic-inorganic composite dispersion (MNC2.5M0.8) was measured using a particle size distribution measurement apparatus (Microtrac UPA 150 available from Nikkiso Co., Ltd.) and an average particle size thus obtained was 70 nm.

The organic-inorganic composite dispersion (MNC2.5M0.8) was pre-treated, dried, and subjected to TEM-EDS mapping measurement with a transmission electron microscope in the same manner as in Example 1. The results of the mapping measurement confirmed that the clay mineral was uniformly dispersed in the particle.

In this reaction system, Ra was 0.20 and the concentration (wt %) of the clay mineral (B) was 1.96(%)<0.87Ra+2.17=2.34.

Example 4

Preparation of Reaction Solution (F) Comprising Monomer (a), Water-Swellable Clay Mineral (B), Water-Soluble Polymerization Initiator (D) and Aqueous Medium (W)

0.32 g of 2-methoxyethyl acrylate (available from Toagosei Co., Ltd.) as a monomer (a), 0.08 g of Laponite XLG (available from Rockwood Additives Ltd.), 50 µl of 2 wt % potassium peroxodisulfate aqueous solution as a water-soluble polymerization initiator (D), 8 µl of N,N,N',N'-tetramethylethylenediamine as a catalyst, and 10 g of water, from which oxygen has been removed by bubbling with nitrogen, as an aqueous medium (W) were uniformly mixed to prepare a reaction solution (F4).

[Preparation of Organic-Inorganic Composite Dispersion]

The reaction solution (F4) was stirred at ambient temperature for 15 hours to prepare a slightly milky white organic-inorganic composite dispersion (MNC1M0.25).

The particle size distribution of the organic-inorganic composite dispersion (MNC1M0.25) was measured using a particle size distribution measurement apparatus (Microtrac UPA 150 available from Nikkiso Co., Ltd.) and an average particle size thus obtained was 60 nm.

The organic-inorganic composite dispersion (MNC1M0.25) was pre-treated, dried, and subjected to TEM-EDS mapping measurement using a transmission electron microscope in the same manner as in Example 1. The results of the mapping measurement confirmed that the clay mineral was uniformly dispersed in the particle.

In this reaction system, Ra was 0.25 and the concentration (wt %) of the clay mineral (B) was 0.79(%)<0.87Ra+2.17=2.39.

Example 5

[Preparation of Reaction Solution (F) Comprising Monomer (a), Water-Swellable Clay Mineral (B), Water-Insoluble Photopolymerization Initiator (D) and Aqueous Medium (W)

0.32 g of 2-methoxyethyl acrylate (available from Toagosei Co., Ltd.) as a monomer (a), 0.16 g of Laponite XLG (available from Rockwood Additives Ltd.), 25 µl of the solution (G1) as a water-insoluble photopolymerization initiator (D), 50 µl of 20 wt % sodium dodecylbenzene sulfonate (available from Wako Pure Chemical Industries, Ltd.) as a surfactant, and 10 g of water as an aqueous medium (W) were uniformly mixed to prepare a reaction solution (F5).

[Preparation of Organic-Inorganic Composite Dispersion]

The reaction solution (F5) was irradiated with ultraviolet rays (with intensity 40 mW/cm$^2$ at 365 nm) for 180 seconds while being stirred with a magnetic stirrer to prepare a slightly milky white organic-inorganic composite dispersion (MNC2M0.25).

The particle size distribution of the organic-inorganic composite dispersion (MNC2M0.25) was measured using a particle size distribution measurement apparatus (Microtrac UPA 150 available from Nikkiso Co., Ltd.) and an average particle size thus obtained was 80 nm.

The organic-inorganic composite dispersion (MNC2M0.25) was dried and subjected to TEM-EDS mapping (analysis for distribution of clay mineral in particles of composite (X)) with a transmission electron microscope (JEM-2200 FS available from JEOL Ltd.). The mapping measurement results confirmed that the clay mineral was uniformly dispersed in the particle.

In this reaction system, Ra was 0.5 and the concentration (wt %) of the clay mineral (B) was 1.57(%)<0.87Ra+2.17=2.61.

[Preparation of Cell Culture Substrate Provided with Dry Film of Organic-Inorganic Composite Dispersion on the Surface]

The organic-inorganic composite dispersion (MNC2M0.25) was applied to the surface of an about 100 µm thick polyethylene terephthalate (PET) film to a thickness of about 100 µm, dried at 50° C. for one hour, washed with sterile water at 50° C. and dried at 50° C. for 2 hours to prepare a cell culture substrate 1. The dry film of the composite (X) was transparent and had a thickness of about 6 µm.

The dry film was cut in a grid with a size of 1×1 mm with a cutter knife, the grid region was strongly pressed with a cellophane tape, the end of the tape was rapidly peeled off at an angle of 45°, and the grid was then observed. The applied film was not detached and exhibited superior adhesion to the substrate.

[Cell Culture Test]

The cell culture substrate 1 was placed in a polystyrene schale with a diameter of 5 cm (Tissue Culture Dish available from AGC Techno Glass Co., Ltd.) and Balb3T3 cells (established mouse fibroblast cell line) were cultured in 5% carbon dioxide at 37° C. using a MEA medium comprising 10% FBS (available from Cell Systems Corporation). On the fourth day, the surface of the cell culture substrate 1 was observed. It could be seen that cells were sufficiently proliferated.

Meanwhile, cell culture tests were performed as illustrated above using only the washed PET film. On the fourth day, the surface of the PET film was observed. As a result, it was confirmed that cells were not seen and not proliferated at all.

As can be seen from this Example, cell culture performance can be imparted to the substrate in which cells cannot be proliferated, by adhering the dry film of the composite (X) of the present invention thereto. Also, the composite film was not detached from PET films and exhibited sufficient adhesion even upon washing with warm water or culturing at 37° C.

Example 6

Preparation of Reaction Solution (F) Comprising Monomer (a), Water-Swellable Clay Mineral (B), Water-Insoluble Photopolymerization Initiator (D) and Aqueous Medium (W)

0.18 g of 2-methoxyethyl acrylate (available from Toagosei Co., Ltd.) as a monomer (a), 0.32 g of Laponite XLG (available from Rockwood Additives Ltd.) as a clay mineral (B), 25 μl of the solution (G1) as a water-insoluble photopolymerization initiator (D) and 10 g of water as an aqueous medium (W) were uniformly mixed to prepare a reaction solution (F6).

[Preparation of Organic-Inorganic Composite Dispersion]

The reaction solution (F6) was irradiated with ultraviolet rays (with intensity 40 mW/cm$^2$ at 365 nm) for 180 seconds while being stirred with a magnetic stirrer to prepare a slightly milky white organic-inorganic composite dispersion (MNC4M0.14).

The particle size distribution of the organic-inorganic composite dispersion (MNC4M0.14) was measured using a particle size distribution measurement apparatus (Microtrac UPA 150 available from Nikkiso Co., Ltd.) and an average particle size thus obtained was 80 nm.

The organic-inorganic composite dispersion (MNC4M0.14) was dried and subjected to TEM-EDS mapping (analysis for distribution of clay mineral in particles of composite (X)) with a transmission electron microscope (JEM-2200 FS available from JEOL Ltd.). The mapping measurement results confirmed that the clay mineral was uniformly dispersed in the particle.

In this reaction system, Ra was 1.8 and the concentration (wt %) of the clay mineral (B) was 3.10(%)<0.87Ra+2.17=3.74.

Example 7

Preparation of Reaction Solution (F) Comprising Monomer (a), Water-Swellable Clay Mineral (B), Water-Insoluble Photopolymerization Initiator (D) and Aqueous Medium (W)

0.9 g of 2-methoxyethyl acrylate (available from Toagosei Co., Ltd.) as a monomer (a), 0.06 g of Laponite XLG (available from Rockwood Additives Ltd.) as a clay mineral (B), 25 μl of the solution (G1) as a water-insoluble photopolymerization initiator (D) and 10 g of water as an aqueous medium (W) were uniformly mixed to prepare a reaction solution (F7).

[Preparation of Organic-Inorganic Composite Dispersion]

The reaction solution (F7) was irradiated with ultraviolet rays (with intensity 40 mW/cm$^2$ at 365 nm) for 180 seconds while being stirred with a magnetic stirrer to prepare a slightly milky white organic-inorganic composite dispersion (MNC0.75M0.7).

The particle size distribution of the organic-inorganic composite dispersion (MNC0.75M0.7) was measured using a particle size distribution measurement apparatus (Microtrac UPA 150 available from Nikkiso Co., Ltd.) and an average particle size thus obtained was 80 nm.

The organic-inorganic composite dispersion (MNC0.75M0.7) was pre-treated, dried and subjected to TEM-EDS mapping measurement using a transmission electron microscope in the same manner as in Example 1. The results of the mapping measurement showed a core-shell structure in which clay minerals was localized at the surface portion of the particle.

In this reaction system, Ra was 0.067 and the concentration (wt %) of the clay mineral (B) was 0.60(%)<12.4Ra+0.05=0.88.

Example 8

Preparation of Reaction Solution (F) Comprising Monomer (a), Water-Swellable Clay Mineral (B), Water-Insoluble Photopolymerization Initiator (D) and Aqueous Medium (W)

0.048 g of 2-methoxyethyl acrylate (available from Toagosei Co., Ltd.) as a monomer (a), 0.48 g of Laponite XLG (available from Rockwood Additives Ltd.) as a clay mineral (B), 25 μl of the solution (G1) as a water-insoluble photopolymerization initiator (D) and 10 g of water as an aqueous medium (W) were uniformly mixed to prepare a reaction solution (F8).

[Preparation of Organic-Inorganic Composite Dispersion]

The reaction solution (F8) was irradiated with ultraviolet rays (with intensity 40 mW/cm$^2$ at 365 nm) for 180 seconds while being stirred with a magnetic stirrer to prepare a slightly milky white organic-inorganic composite dispersion (MNC6M0.04).

The particle size distribution of the organic-inorganic composite dispersion (MNC6M0.04) was measured using a particle size distribution measurement apparatus (Microtrac UPA 150 available from Nikkiso Co., Ltd.) and average particle sizes thus obtained were 80 nm and 2.5 μm.

The organic-inorganic composite dispersion (MNC6M0.04) was pre-treated, dried and subjected to TEM-EDS mapping measurement with a transmission electron microscope in the same manner as in Example 1. The results of the mapping measurement confirmed that the clay mineral was uniformly dispersed in the particle.

In this reaction system, Ra was 10 and the concentration (wt %) of the clay mineral (B) was 4.58(%)<0.87Ra+2.17=10.87.

Example 9

Preparation of Reaction Solution (F) Comprising Monomer (a), Water-Swellable Clay Mineral (B), Water-Soluble Polymerization Initiator (D) and Aqueous Medium (W)

0.026 g of 2-methoxyethyl acrylate (available from Toagosei Co., Ltd.) as a monomer (a), 0.02 g of Laponite XLG (available from Rockwood Additives Ltd.) as a clay mineral (B), 50 μl of 2 wt % potassium peroxodisulfate aqueous solution as a water-soluble polymerization initiator (D), 8 μl of N,N,N',N'-tetramethylethylenediamine as a catalyst, and 10 g of water, from which oxygen had been removed through bubbling with nitrogen, as an aqueous medium (W) were uniformly mixed to prepare a reaction solution (F9).

[Preparation of Organic-Inorganic Composite Dispersion]

The reaction solution (F9) was stirred at ambient temperature for 15 hours to prepare a slightly milky white organic-inorganic composite dispersion (MNC0.25M0.02).

The particle size distribution of the organic-inorganic composite dispersion (MNC0.25M0.02) was measured using a particle size distribution measurement apparatus (Microtrac UPA 150 available from Nikkiso Co., Ltd.) and an average particle sizes thus obtained was 160 nm.

The organic-inorganic composite dispersion (MNC0.25M0.02) was pre-treated, dried and subjected to TEM-EDS mapping measurement with a transmission electron microscope in the same manner as in Example 1. The results of the mapping measurement confirmed that the clay mineral was uniformly dispersed in the particle.

In this reaction system, Ra was 0.77 and the concentration (wt %) of the clay mineral (B) was 0.20(%)<0.87Ra+ 2.17=2.84.

Example 10

In this Example, a dispersion of particles of a composite (X) composed of a copolymer (A) of a monomer of Formula (1) with another monomer and a clay mineral (B) was prepared.
[Preparation of Reaction Solution (F) Comprising Monomer (a), Another Monomer, Water-Swellable Clay Mineral (B), Water-Insoluble Photopolymerization Initiator (D), and Aqueous Medium (W)]

0.2944 g of 2-methoxyethyl acrylate (available from Toagosei Co., Ltd.) as a monomer (a), 0.0964 g of methoxy polyethylene glycol acrylate "trade name: NKesterAM-90G" (available from Shin-Nakamura Chemical Co., Ltd.) as another monomer, 0.02 g of Laponite XLG (available from Rockwood Additives Ltd.) as a clay mineral (B), 25 μl of the solution (G1) as a water-insoluble photopolymerization initiator (D) and 10 g of water as an aqueous medium (W) were uniformly mixed to prepare a reaction solution (F10).
[Preparation of Organic-Inorganic Composite Dispersion]

The reaction solution (F10) was irradiated with ultraviolet rays (with intensity 40 mW/cm$^2$ at 365 nm) for 180 seconds while being stirred with a magnetic stirrer to prepare a slightly milky white organic-inorganic composite dispersion (M/AM90G8NC0.25M0.25).

The particle size distribution of the organic-inorganic composite dispersion (M/AM90G8NC0.25M0.25) was measured using a particle size distribution measurement apparatus (Microtrac UPA 150 available from Nikkiso Co., Ltd.) and an average particle size thus obtained was 70 nm.

The organic-inorganic composite dispersion (M/AM90G8NC0.25M0.25) was pre-treated, dried and subjected to TEM-EDS mapping measurement with a transmission electron microscope in the same manner as in Example 1. The results of the mapping measurement confirmed that the clay mineral was uniformly dispersed in the particle.

In this reaction system, Ra was 0.05 and the concentration (wt %) of the clay mineral (B) was 0.20(%)<12.4Ra+ 0.05=0.67.

Example 11

Preparation of Dry Film of Composite (X)

The organic-inorganic composite dispersion (MNC2M0.25) prepared in Example 5 was charged to a liquid thickness of 2 mm in a polypropylene vessel and dried at 50° C. for 5 hours to obtain a colorless transparent flexible film with a thickness of about 80 μm.

The film was analyzed using a tensile tester (AGS-H type available from Shimadzu Corporation). As a result, the stress at break was 15 MPa, and strain at break was 36%.

Example 12

Preparation of Antifogging Applied Film of Composite (X)

To the organic-inorganic composite dispersion (MNC0.5M1) prepared in the Example 1, poly(N-isopropylacrylamide) (average molecular weight of about 250,000; available from Showa Chemical Co., Ltd.) was added to an amount of 1.5 wt %, then uniformly mixed. The mixture was applied to a thickness of about 50 μm on a glass plate, then dried at 80° C. for 60 minutes to prepare an antifogging applied film 1. The dried film of composite (X) had a thickness of about 5 μm.

The applied film was cut in a grid with a size of 1×1 mm with a cutter knife, the grid region was strongly pressed with a cellophane tape, the end of the tape was rapidly peeled off at an angle of 45°, and the grid was then observed. The applied film was not detached and exhibited superior adhesion to the substrate.

Also, this applied film was exposed to water vapor generated in water at 50° C. for about one minute (the distance between the applied film and the water surface was about 5 cm). As a result, the applied film was not foggy.

Also, this applied film was dipped in water at 50° C. for 24 hours, dried at ambient temperature, then exposed to the water vapor for about one minute. As a result, the applied film was not foggy.

As can be seen from this Example, the applied film of composite (X) comprising a hydrophilic polymer (polyacrylic acid) had superior adhesion to the substrate and antifogging properties which remained even after washing with hot water.

Example 13

Preparation of Reaction Solution (F) Comprising Monomer (a), Silica (B), Water-Insoluble Photopolymerization Initiator (D) and Aqueous Medium (W)

0.32 g of 2-methoxyethyl acrylate (available from Toagosei Co., Ltd.) as a monomer (a), 0.1 g of Snotex 20 (20 wt % colloidal silica aqueous solution available from Nissan Chemical Industries, Ltd.) (solid content: 0.02 g) as a silica (B), 25 μl of the solution (G1) as a water-insoluble photopolymerization initiator (D) and 10 g of water as an aqueous medium (W) were uniformly mixed to prepare a reaction solution (F13).
[Preparation of Organic-Inorganic Composite Dispersion]

The reaction solution (F13) was irradiated with ultraviolet rays (with intensity 40 mW/cm$^2$ at 365 nm) for 180 seconds while being stirred with a magnetic stirrer to prepare a slightly milky white organic-inorganic composite dispersion (13).

The particle size distribution of the organic-inorganic composite dispersion (13) was measured using a particle size distribution measurement apparatus (Microtrac UPA 150 available from Nikkiso Co., Ltd.) and an average particle size thus obtained was 50 nm.

The organic-inorganic composite dispersion (13) was pre-treated, dried and subjected to TEM-EDS mapping measurement with a transmission electron microscope in the same manner as in Example 1. The results of the mapping measurement confirmed that silica was uniformly dispersed in the particle.

In this reaction system, Ra was 0.0625 and the concentration (wt %) of the clay mineral (B) was 0.20(%)<12.4Ra+ 0.05=0.83.

Example 14

Preparation of Patterned Dry Film and Culture Substrate

The dispersion (13) of Example 13 was applied to a 1 mm thick polystyrene substrate in the form of lines with a thickness of 100 μm and a gap of about 200 μm using a single nozzle pulse injector (available from Cluster Technology Co., Ltd.), and dried to air to obtain a patterned dry film of composite (X) 14.

Figure 4:
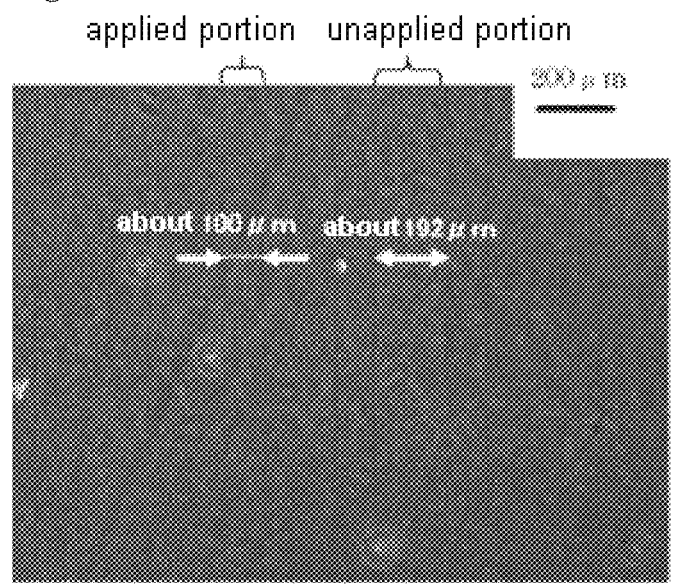
FIG. 4 is an optical micrograph of cell culture substrate 14 (Example 14) obtained by applying an organic-inorganic composite dispersion (13) in a line pattern.

Subsequently, the dry film was washed with sterile water and dried in a sterilization bag at 40° C. for 5 hours to obtain a cell culture substrate 14. This cell culture substrate 14 was observed with an optical microscope. Line pattern of about 100 μm line thickness formed on the polystyrene substrate was observed. The gap between adjacent lines was about 192 μm (FIG. 4).

Also, for comparison, a predetermined amount of the dispersion (13) was placed on a polystyrene substrate, thinly applied on the substrate surface at 2,000 rpm using a spin coater, and dried in a hot air drier at 80° C. for 10 min. Then, the polystyrene substrate was washed with sterile water and dried in a sterilization bag at 40° C. for 5 hours to obtain a cell culture substrate 14'.

[Culturing of Balb3T3 Cells (Mouse Tumor Fibroblast Cells)]

Figure 5:
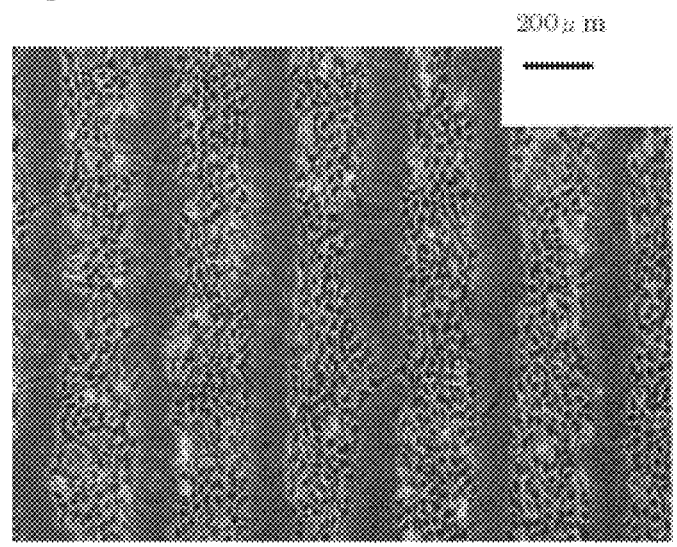
FIG. 5 is an optical micrograph of cells cultured on a cell culture substrate 14 for 22 hours.
Figure 6:
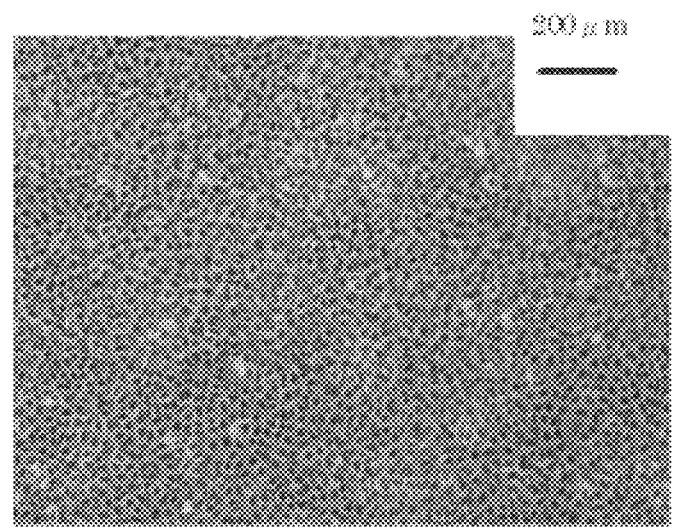
FIG. 6 is an optical micrograph of cells cultured on a cell culture substrate 14 for 46 hours.

The cell culture substrate 14 thus obtained was placed in a 60 mm polystyrene schale (60 mm/non-treated dish available from Asahi Techno Glass Corporation), a predetermined amount of Dulbecco's modified Eagle's medium (DMEM) supplemented with 10% FBS (available from Nissui Pharmaceutical Co., Ltd.) was added thereto, Balb3T3 cells were seeded (at a concentration of $1.0 \times 10^4$ cell/cm$^2$) and cultured in 5% carbon dioxide at 37° C. Cells proliferated for 22 hours were observed with a microscope. The results indicated that the cells were linearly proliferated (FIG. 5). Also, the cells proliferated for 46 hours were observed with a microscope. The results indicated that the applied region and the unapplied region were substantially entirely covered with cells (FIG. 6). Then, the medium was replaced with a 4° C. medium and was repeatedly absorbed and discharged with a spoid (called "pipetting"). As a result, cells were detached in the form of a thin layer from the cell culture substrate 14. The area of the detached cells was about 95% of the total area of the proliferated cells before detachment.

Meanwhile, similarly, Balb3T3 cells were cultured for 46 hours using the cell culture substrate 14'. As a result, the overall surface of the applied region was covered with cells. Then, the medium was replaced with a 4° C. medium and pipetting was repeated several times with a spoid. As a result, cells were substantially not detached.

Also, similarly, Balb3T3 cells were cultured using the polystyrene substrate (unapplied one) and the cells were almost not proliferated at all. As a result, the polystyrene substrate is a material which cannot culture the seeded cells.

It can be seen from Example 14 that by applying the dispersion (13) in a line pattern, similar to the cell culture substrate 14' which was entirely applied with the dispersion (13), cells can be proliferated throughout the unapplied and applied regions, and proliferated cells are attached only at the applied region of the support, thus readily detached by external shock (cooling, pipetting).

Example 15

Preparation of Reaction Solution (F) Comprising Monomer (a), Another Monomer, Water-Swellable Clay Mineral (B), Water-Insoluble Photopolymerization Initiator (D), and Aqueous Medium (W)

0.27 g of 2-methoxyethyl acrylate (available from Toagosei Co., Ltd.) as a monomer (a), 0.18 g of methoxy polyethylene glycol acrylate "trade name: NKesterAM-90G" (available from Shin-Nakamura Chemical Co., Ltd.: the compound of Formula (1) wherein $R_1$ is a hydrogen atom, $R_2$ is an ethylene group, $R_3$ is a methyl group, and n is an integer of 9) as an another monomer, 0.02 g of Laponite XLG (available from Rockwood Additives Ltd.) as a clay mineral (B), 25 μl of the solution (G1) as a water-insoluble photopolymerization initiator (D) and 10 g of water as an aqueous medium (W) were uniformly mixed to prepare a reaction solution (F15).

[Preparation of Organic-Inorganic Composite Dispersion]

The reaction solution (F15) was irradiated with ultraviolet rays (with intensity 40 mW/cm$^2$ at 365 nm) for 180 seconds while being stirred with a magnetic stirrer to prepare a slightly milky white organic-inorganic composite dispersion (15).

The particle size distribution of the organic-inorganic composite dispersion (15) was measured using a particle size distribution measurement apparatus (Microtrac UPA 150 available from Nikkiso Co., Ltd.) and an average particle size thus obtained was 70 nm.

The organic-inorganic composite dispersion (15) was pretreated, dried and subjected to TEM-EDS mapping measurement using a transmission electron microscope in the same manner as in Example 1. The mapping measurement results confirmed that the clay mineral was uniformly dispersed in the particle. In this reaction system, Ra was 0.074 and the concentration (wt %) of the clay mineral (B) was 0.20(%) <12.4Ra+0.05=0.97.

[Preparation of Cell Culture Substrate]

The dispersion (15) was placed in a polystyrene schale (60 mm/non-treated dish, available from Asahi Techno Glass Corporation), thinly applied to the schale surface at 2,000 rpm using a spin coater, and dried in a hot air drier at 80° C. for 10 minutes to obtain a dry film. Then, the schale was washed with sterile water and dried in a sterilization bag at 40° C. for 5 hours to obtain a cell culture substrate 15.

The dry film was cut into a grid with a size of 1×1 mm with a cutter knife, the grid region was strongly pressed with a cellophane tape, the end of the tape was rapidly peeled off at an angle of 45°, and the grid was then observed. Results indicated that the applied film was not detached and exhibited superior adhesion to the substrate.

[Culturing of Normal Human Dermal Fibroblast Cells]

A predetermined amount of CS-C complete medium (available from Cell Systems Corporation) was added to the cell culture substrate 15 thus obtained, and normal human dermal fibroblast cells were seeded (at a concentration of $1.2 \times 10^4$ cell/cm$^2$) and cultured in 5% carbon dioxide at 37° C. After being proliferated for 5 days, the cells were observed with a microscope. The observance results indicated that one surface of schale was covered with cells. Then, the medium in the schale was removed by aspiration, a 4° C. medium was added thereto, then allowed to stand for a predetermined period to induce natural detachment of the proliferated cells. As a result, the cells were slowly detached and substantially all cells were detached in the form of thin film in about 20 minutes.

It can be seen from Example 15 that, at 37° C., the surface to which the dispersion (15) was applied exhibited adhesion to cells and cells were proliferated, while at a decreased temperature, cells were naturally detached from the surface of the applied film.

Comparative Example 1

Preparation of Dispersion (L) Comprising Monomer (a), Water-Swellable Clay Mineral (B), Water-Soluble Polymerization Initiator (D) and Aqueous Medium (W)

1.8 g of 2-methoxyethyl acrylate (available from Toagosei Co., Ltd.) as a monomer (a), 0.018 g of Laponite XLG (available from Rockwood Additives Ltd.) as a clay mineral (B), 50 µl of 2 wt % potassium peroxodisulfate aqueous solution as a water-soluble polymerization initiator (D), 8 µl of N,N,N',N'-tetramethylethylenediamine as a catalyst, and 10 g of water, from which oxygen had been removed through bubbling with nitrogen, as an aqueous medium (W) were uniformly mixed to prepare a reaction solution (F1C).

The reaction solution (F1C) was stirred at ambient temperature for 15 hours. As a result, a heterogeneous dispersion comprising partially large masses of gel was obtained. The large masses of gel present in the heterogeneous dispersion were not dissolved or dispersed even after stirring of the dispersion for a long time.

In this reaction system, Ra was 0.01 and the concentration (wt %) of the clay mineral (B) was =0.18>12.4Ra+0.05=0.17.

Comparative Example 2

Preparation of Dispersion (L) Comprising Monomer (a), Water-Swellable Clay Mineral (B), Water-Soluble Polymerization Initiator (D) and Aqueous Medium (W)

1.7 g of 2-methoxyethyl acrylate (available from Toagosei Co., Ltd.) as a monomer (a), 0.05 g of Laponite XLG (available from Rockwood Additives Ltd.) as a clay mineral (B), 50 µl of 2 wt % potassium peroxodisulfate aqueous solution as a water-soluble polymerization initiator (D), 8 µl of N,N,N',N'-tetramethylethylenediamine as a catalyst, and 10 g of water, from which oxygen had been removed through bubbling with nitrogen, as an aqueous medium (W) were uniformly mixed to prepare a reaction solution (F2C).

The reaction solution (F2C) was stirred at ambient temperature for 15 hours. As a result, a heterogeneous dispersion comprising partially large masses of gel was obtained. The large masses of gel present in the heterogeneous dispersion were not dissolved or dispersed even after stirring of the dispersion for a long time.

In this reaction system, Ra was 0.03 and the concentration (wt %) of the clay mineral (B) was 0.50>12.4Ra+0.05=0.42.

Comparative Example 3

Preparation of Dispersion (L) Comprising Monomer (a), Water-Swellable Clay Mineral (B), Water-Soluble Polymerization Initiator (D) and Aqueous Medium (W)

A reaction solution (F3C) was prepared in the same manner as in Comparative Example 2 except that 1.28 g of 2-methoxyethyl acrylate (available from Toagosei Co., Ltd.) was used as a monomer (a), and 0.08 g of Laponite XLG (available from Rockwood Additives Ltd.) was used as a clay mineral (B).

The reaction solution (F3C) was stirred at ambient temperature for 15 hours. As a result, the reaction solution was almost entirely gelled. The gel was not dissolved or dispersed and was maintained even when added to a large amount of water.

In this reaction system, Ra was 0.06 and the concentration (wt %) of the clay mineral (B) was 0.79=12.4Ra+0.05=0.79.

Comparative Example 4

Preparation of Dispersion (L) Comprising Monomer (a), Water-Swellable Clay Mineral (B), Water-Soluble Polymerization Initiator (D) and Aqueous Medium (W)

A reaction solution (F4C) was prepared in the same manner as in Comparative Example 2 except that 1.28 g of 2-methoxyethyl acrylate (available from Toagosei Co., Ltd.) was used as a monomer (a), and 0.16 g of Laponite XLG (available from Rockwood Additives Ltd.) was used as a clay mineral (B).

The reaction solution (F4C) was stirred at ambient temperature for 15 hours. As a result, the reaction solution was almost entirely gelled. The gel was not dissolved or dispersed and was maintained even when added to a large amount of water.

In this reaction system, Ra was 0.125 and the concentration (wt %) of the clay mineral (B) was 1.60=12.4Ra+0.05=1.60.

Comparative Example 5

Preparation of Reaction Solution (L) Comprising Monomer (a), Water-Swellable Clay Mineral (B), Water-Insoluble Photopolymerization Initiator (D) and Aqueous Medium (W)

1.28 g of 2-methoxyethyl acrylate (available from Toagosei Co., Ltd.) as a monomer (a), 0.24 g of Laponite XLG (available from Rockwood Additives Ltd.) as a clay mineral (B), 25 µl of the solution (G1) as a water-insoluble polymerization initiator (D) and 10 g of water as an aqueous medium (W) were uniformly mixed to prepare a reaction solution (F5C).

The reaction solution (F5C) was irradiated with ultraviolet rays (with intensity 40 mW/cm$^2$ at 365 nm) for 180 seconds while being stirred with a magnetic stirrer. As a result, the reaction solution (F5C) was entirely gelled. The gel was not dissolved or dispersed and was maintained even when added to a large amount of water.

In this reaction system, Ra was 0.19 and the concentration (wt %) of the clay mineral (B) was 2.34%=0.87Ra+2.17=2.34.

Comparative Example 6

Preparation of Dispersion (L) Comprising Monomer (a), Water-Swellable Clay Mineral (B), Water-Insoluble Photopolymerization Initiator (D) and Aqueous Medium (W)

0.22 g of 2-methoxyethyl acrylate (available from Toagosei Co., Ltd.) as a monomer (a), 0.40 g of Laponite XLG (available from Rockwood Additives Ltd.) as a clay mineral (B), 25 µl of the solution (G1) as a water-insoluble polymerization initiator (D) and 10 g of water as an aqueous medium (W) were uniformly mixed to prepare a reaction solution (F6C).

The reaction solution (F6C) was irradiated with ultraviolet rays (with intensity 40 mW/cm$^2$ at 365 nm) for 180 seconds while being stirred with a magnetic stirrer. As a result, the reaction solution (F6C) was entirely gelled. The gel was not dissolved or dispersed and was maintained even when added to a large amount of water.

In this reaction system, Ra was 1.82 and the concentration (wt %) of the clay mineral (B) was 3.85%>0.87Ra+2.17=3.75.

It can be seen from the aforementioned Examples and Comparative Examples that the organic-inorganic composite dispersion of the present invention enables easy control of particle size and exhibits superior dispersion stability and excellent adhesion to substrates such as PET or glasses. Also, the dry film formed by drying the composite dispersion exhibited high strength, flexibility and transparency and excellent cell culture performance, biocompatibility and antifogging properties. Also, according to the preparation method, a clay mineral and an organic polymer can be compounded in different structures in a wide range of clay mineral content, and organic-inorganic composite dispersions with excellent dispersion stability or film formability can be readily prepared in an extremely short time without removing oxygen.

Examples and Comparative Examples for Cell Culture Substrates Comprising Polymer (B) Having Lower Critical Solution Temperature The following Examples and Comparative Examples relate to cell culture substrates comprising a polymer (B) having a lower critical solution temperature.

Example 16

In this example, a cell culture substrate was prepared by the first preparation method.
[Preparation of Reaction Solution Comprising Monomer (a), Inorganic Material (C) and Aqueous Medium (W)]
 0.6 g of 2-methoxyethyl acrylate (available from Toagosei Co., Ltd.) as a monomer (a), 0.3 g of Laponite XLG (available from Rockwood Additives Ltd.) as an inorganic material (C) and 20 g of water as an aqueous medium (W) were uniformly mixed to prepare a reaction solution (F17).
[Preparation of Solution of Polymerization Initiator (D) in Solvent (E)]
 9.8 g of 2-propanol as a solvent (E) and 0.2 g of hydroxycyclohexyl phenyl ketone "Irgacure 184" (available from Ciba-Geigy Ltd.) as a polymerization initiator (D) were uniformly mixed to prepare a solution (S1).
[Preparation of Dispersion (L) of Composite (X) (First Step)]
 50 µl of the solution (S1) was added to the entire amount of the reaction solution (F17) and uniformly dispersed. The dispersion was irradiated with ultraviolet rays (with intensity 40 mW/cm$^2$ at 365 nm) for 180 seconds to prepare a milky white dispersion (L1) of composite (X).
 In this reaction system, Ra was 0.5 and the concentration (wt %) of the inorganic material (C) was 1.48(%)<0.87Ra+2.17=2.61.
[Preparation of Thin Layer of Composite (X) (Second Step)]
 The dispersion (L1) of composite (X) was placed in a polystyrene schale with a diameter of 50 mm (available from Advantec Toyo Kaisha, Ltd., PD-50K), thinly applied to the schale surface at 2,000 rpm using a spin coater, and dried in a hot air drier at 80° C. for 10 minutes to obtain a thin layer of composite (X).
[Application of Solution of Polymerization Initiator (D) in Solvent (E) (Third Step)]
 Next, the solution (S1) was placed in the schale and thinly applied at 2000 rpm with a spin coater, then allowed to stand at ambient temperature for 5 minutes to volatilize ethanol, thereby the polymerization initiator (D) was applied to the surface of the thin layer of composite (X).
[Preparation of Cell Culture Substrate (Fourth Step)]
 2 ml of 10 wt % aqueous solution of N-isopropylacrylamide (monomer (b), available from Kohjin Co., Ltd.) was placed in the schale and polymerized by irradiation of ultraviolet rays (with intensity 40 mW/cm$^2$ at 365 nm) for 60 seconds. Then, the schale was washed with sterile water and dried in a sterilization bag 40° C. for 5 hours to obtain a cell culture substrate 16.
 The dry film was cut into a grid with a size of 1×1 mm using a cutter knife, the grid region was firmly pressed against a tape, the end of the tape was rapidly peeled off at an angle of 45°, and the grid was then observed. The applied film was not detached and exhibited superior adhesion to the substrate.
[Culturing of Normal Human Dermal Fibroblast Cells]
 A predetermined amount of CS-C complete medium (available from Cell Systems Corporation) was added to the cell culture substrate 16 thus obtained, and normal human dermal fibroblast cells were seeded (at a concentration of 1.2×10$^4$ cell/cm$^2$) and cultured in 5% carbon dioxide at 37° C. Upon confirming sufficient proliferation of the cell, the medium (at 37° C.) was removed by aspiration, a 4° C. medium was added thereto, then allowed to stand for a predetermined period to naturally detach proliferated cells. A ratio of detached cell area and total area of the proliferated cells before detachment was calculated. Also, the time required for detachment was recorded (Table 1, cell detachment collection=93%, the time required for detachment=18 minutes).

Example 17

In this example, a cell culture substrate was prepared by the first preparation method.
 A cell culture substrate 17 was prepared in the same manner as in Example 16 except that 17 wt % N-isopropylacrylamide aqueous solution was used as the monomer (b) in the fourth step.
 The adhesion of the dry film was tested in the same manner as in Example 16. As a result, it was confirmed that the applied film was not detached and exhibited superior adhesion to the substrate.
[Culturing of Normal Human Dermal Fibroblast Cells]
 The normal human dermal fibroblast cells were cultured in the same manner as in Example 16. Upon confirming sufficient proliferation of the cell, the medium (at 37° C.) was replaced with 4° C. medium, then allowed to stand for a predetermined period to naturally detach the proliferated cells. A ratio of detached cell area and total area of the proliferated cells before detachment was calculated. Also, the time required for detachment was recorded (Table 1, cell detachment collection=98%, the time required for detachment=10 minutes).
 It can be seen from Examples 16 and 17 that cell detachment can be improved by increasing the concentration of the monomer (b).

Example 18

In this example, a cell culture substrate was prepared by the second preparation method.
[Preparation of Reaction Solution Comprising Monomer (a), Inorganic Material (C) and Aqueous Medium (W)]
 1.28 g of 2-methoxyethyl acrylate (available from Toagosei Co., Ltd.) as a monomer (a), 0.24 g of water-swellable clay mineral Laponite XLG (available from Rockwood Additives Ltd.) as an inorganic material (C), and 10 g of water as an aqueous medium (W) were uniformly mixed to prepare a reaction solution (F18).
[Preparation of Solution of Polymerization Initiator (D) in Solvent (E)]
 The same solution (S1) as in Example 16 was used.
[Preparation of Thin Layer of Composite (X) (First Step)]
 50 µl of the solution (S1) was added to the entire amount of the reaction solution (F18) and uniformly dispersed. The dispersion was placed in a polystyrene schale with a diameter of 50 mm (available from Advantec Toyo Kaisha, Ltd., PD-50K), thinly applied to the schale surface at 2,000 rpm using a spin coater, and irradiated with ultraviolet rays (with intensity 40 mW/cm² at 365 nm) for 180 seconds to obtain a thin layer of composite (X).
[Application of Solution of Polymerization Initiator (D) in Solvent (E)] (Second Step)

The solution (S1) was placed in the schale and thinly applied at 2000 rpm with a spin coater, then allowed to stand at ambient temperature for 5 minutes in order to evaporate ethanol. As a result, the polymerization initiator (D) was applied.
[Preparation of Cell Culture Substrate (Third Step)]

2 ml of 15 wt % aqueous solution of N-isopropylacrylamide (monomer (b), available from Kohjin Co., Ltd.) was placed in the schale and polymerized by irradiation of ultraviolet rays (with intensity 40 mW/cm² at 365 nm) for 60 seconds. Then, the schale was washed with sterile water and dried in a sterilization bag at 40° C. for 5 hours to obtain a cell culture substrate 18.

Adhesion of the dry film was tested in the same manner as in Example 16. As a result, it was confirmed that the applied film was not detached and exhibited superior adhesion to the substrate.
[Culturing of Normal Human Dermal Fibroblast Cells]

Normal human dermal fibroblast cells were cultured using the cell culture substrate 18 in the same manner as in Example 16. Upon confirming sufficient proliferation of the cell, the medium (at 37° C.) was replaced with a 4° C. medium, then allowed to stand for a predetermined period to naturally detach the proliferated cells. A ratio of detached cell area and total area of the proliferated cells before detachment was calculated. Also, the time required for detachment was recorded (Table 1, cell detachment collection=100%, the time required for detachment=12 minutes).

Example 19

In this Example, a cell culture substrate was prepared by the second preparation method.

A cell culture substrate 19 was prepared in the same manner as in Example 18, except that 3 wt % aqueous solution of N-isopropylacrylamide was used as the monomer (b) in the third step.

The adhesion of the dry film was tested in the same manner as in Example 16. As a result, it was confirmed that the applied film was not detached and exhibited superior adhesion to the substrate.
[Culturing of Normal Human Dermal Fibroblast Cells]

Normal human dermal fibroblast cells were cultured using the cell culture substrate 19 in the same manner as in Example 16. Upon confirming sufficient proliferation of the cell, the medium (at 37° C.) was replaced with a 4° C. medium, then allowed to stand for a predetermined period to naturally detach the proliferated cells. A ratio of detached cell area and total area of the proliferated cells before detachment was calculated. Also, the time required for detachment was recorded (Table 1, cell detachment collection=78%, the time required for detachment=30 minutes).

It can be seen from Examples 18 and 19 that cell detachment was varied by varying the concentration of the monomer (b).

Example 20

In this Example, a cell culture substrate was prepared by the third preparation method.
[Preparation of Reaction Solution Comprising Monomer (a), Inorganic Material (C) and Aqueous Medium (W)]

0.32 g of 2-methoxyethyl acrylate (available from Toagosei Co., Ltd.) as a monomer (a), 0.08 g of water-swellable clay mineral Laponite XLG (available from Rockwood Additives Ltd.) as an inorganic material (C), 100 µl of 20 wt % sodium dodecylbenzene sulfonate (available from Wako Pure Chemical Industries, Ltd.) aqueous solution as a surfactant, and 10 g of water as an aqueous medium (W) were uniformly mixed to prepare a reaction solution (F20).
[Preparation of Solution of Polymerization Initiator (D) in Solvent (E)]

The same solution (S1) as in Example 16 was used.
[Preparation of Dispersion (L) of Composite (X) (First Step)]

30 µl of the solution (S1) was added to the entire amount of the reaction solution (F20) and uniformly dispersed. The dispersion was irradiated with ultraviolet rays (with intensity 40 mW/cm² at 365 nm) for 180 seconds to obtain a milky white dispersion (L2) of composite (X).

In this reaction system, Ra was 0.25 and the concentration (wt %) of the inorganic material (C) was 0.79(%)<0.87Ra+2.17=2.39.
[Preparation of Polymer (B) Aqueous Solution]

1.7 g of N-isopropylacrylamide (available from Kohjin Co., Ltd.) as a monomer (b), 10 g of water and 140 µl of the solution (S1) were mixed and irradiated with ultraviolet rays (with intensity 40 mW/cm² at 365 nm) for 180 sec while cooling a glass vessel comprising the solution (at about 10° C.) to prepare a poly(N-isopropylacrylamide) aqueous solution. 5 g of water was further added to the solution, which was then uniformly mixed. The viscosity of the resulting solution was measured using a DIGITAL VISCOMATE viscometer (MODEL VM-100A, available from Yamaichi Denki co., Ltd.). The viscosity thus obtained was 368 mPa·s. Upon viscosity measurement, the solution temperature was 24.2° C.

Also, the weight average molecular weight (Mw) of this poly(N-isopropylacrylamide) measured using a Shodex GPC System-21 apparatus (available from Showa Denko K.K.) was $3.40 \times 10^6$. The solvent used for measurement was an N,N-dimethylformamide (DMF) solution comprising 10 mmol/L LiBr. The polystyrene standard materials used for calculation of molecular weight were STANDARD SH-75 and SM-105 kits (available from Showa Denko K.K.).
[Preparation of Cell Culture Substrate (Second Step)]

1.0 g of the poly(N-isopropylacrylamide) aqueous solution (solid content: 0.1 g) was added to the entire amount of the dispersion (L2) and uniformly mixed. The obtained mixture was placed in a 60 mm polystyrene schale (60 mm/non-treated dish, available from Asahi Techno Glass Corporation), thinly applied to the schale surface at 2,000 rpm using a spin coater, and dried in a hot air drier at 80° C. for 10 min. Then, the schale was washed with sterile water and dried in a sterilization bag 40° C. for 5 hours to obtain a cell culture substrate 20.

The adhesion of the dry film was tested in the same manner as in Example 16. As a result, it was confirmed that the applied film was not detached and exhibited superior adhesion to the substrate.
[Culturing of Normal Human Dermal Fibroblast Cells]

Normal human dermal fibroblast cells were cultured using the cell culture substrate 20 in the same manner as in Example 16. Upon confirming sufficient proliferation of the cell, the medium (at 37° C.) was replaced with a 4° C. medium, then allowed to stand for a predetermined period to naturally detach the proliferated cells. A ratio of detached cell area and total area of the proliferated cells before detachment was calculated and the time required for detachment was recorded (Table 1, cell detachment collection=100%, the time required for detachment=7 minutes).

Example 21

In this Example, a cell culture substrate was prepared by the third preparation method.

A cell culture substrate 21 was prepared in the same manner as in Example 20, except that 0.7 g of the poly(N-isopropylacrylamide) aqueous solution was used in the second step.

The adhesion of the dry film was tested in the same manner as in Example 16. As a result, it was confirmed that the applied film was not detached and exhibited superior adhesion to the substrate.

[Culturing of Normal Human Dermal Fibroblast Cells]

Normal human dermal fibroblast cells were cultured using the cell culture substrate 21 in the same manner as in Example 16. Upon confirming sufficient proliferation of the cell, the medium (at 37° C.) was replaced with a 4° C. medium, then allowed to stand for a predetermined period to naturally detach the proliferated cells. A ratio of detached cell area and total area of the proliferated cells before detachment was calculated. Also, the time required for detachment was recorded (Table 1, cell detachment collection=100%, the time required for detachment=15 minutes).

It can be seen from Examples 20 and 21 that cell detachment was changed by varying the amount of poly(N-isopropylacrylamide) aqueous solution.

Example 22

In this Example, a cell culture substrate was prepared by the third prepraration method.

[Preparation of Polymer (B) Aqueous Solution]

0.57 g of N-isopropylacrylamide (available from Kohjin Co., Ltd.) as a monomer (b) was mixed with 100 g of water, the resulting mixture was degassed under vacuum to sufficiently remove oxygen from the aqueous solution, 0.1 g of $K_2S_2O_8$ (potassium peroxodisulfate, manufactured by Wako Pure Chemical Industries, Ltd.) as an initiator and 80 µl of N,N,N',N'-tetramethylethylenediamine (available from Kao Corporation) as a catalyst were added thereto, and the resulting mixture was allowed to stand at 20° C. for 20 hours to obtain a poly(N-isopropylacrylamide) aqueous solution (6). The aqueous solution was heated to 50° C. to precipitate poly(N-isopropylacrylamide), the precipitate was washed with 50° C. ultrapure water and dried at 80° C. for 6 hours to prepare solid poly(N-isopropylacrylamide).

The weight average molecular weight (Mw) of this poly (N-isopropylacrylamide) measured using a Shodex GPC System-21 apparatus (available from Showa Denko K.K.) was $6.0 \times 10^4$. The solvent used for measurement was a N,N-dimethylformamide (DMF) solution comprising 10 mmol/L LiBr. The polystyrene standard materials used for calculation of molecular weight were STANDARD SH-75 and SM-105 kits (available from Showa Denko K.K.).

[Preparation of Cell Culture Substrate (Second Step)]

0.1 g of the solid poly(N-isopropylacrylamide) was added to the entire amount of the dispersion (L2) of Example 20 and uniformly mixed. The obtained mixture was placed in a 60 mm polystyrene schale (60 mm/non-treated dish, available from Asahi Techno Glass Corporation), thinly applied to the schale surface at 2,000 rpm using a spin coater, and dried in a hot air drier at 80° C. for 10 min. Then, the schale was washed with sterile water and dried in a sterilization bag 40° C. for 5 hours to obtain a cell culture substrate 22.

The adhesion of the dry film was tested in the same manner as in Example 16. As a result, the applied film was not detached and exhibited superior adhesion to the substrate.

[Culturing of Normal Human Dermal Fibroblast Cells]

Normal human dermal fibroblast cells were cultured using the cell culture substrate 22 in the same manner as in Example 16. Upon confirming sufficient proliferation of the cell, the medium (at 37° C.) was replaced with a 4° C. medium, then allowed to stand for a predetermined period to naturally detach the proliferated cells. A ratio of detached cell area and total area of the proliferated cells before detachment was calculated. Also, the time required for detachment was recorded (Table 1, cell detachment collection=79%, the time required for detachment=29 minutes).

It can be seen from Examples 20 and 22, cell detachment performance (the time required for detachment) was varied by using same amount (0.1 g) of poly(N-isopropylacrylamide) and varying the molecular weight of poly(N-isopropylacrylamide).

Example 23

In this Example, a patterned cell culture substrate was prepared by the third preparation method.

0.1 g of the poly(N-isopropylacrylamide) aqueous solution of Example 20 was added to the entire amount of the dispersion (L2) of Example 20 and uniformly mixed. The mixture was applied to a 1 mm thick polystyrene substrate in the form of cicles (dots) with a diameter of 30 µm and a gap of about 20 µm using a single nozzle pulse injector (available from Cluster Technology Co., Ltd.). Then, the polystyrene substrate was dried in a hot air drier at 80° C. for 10 min, washed with sterile water and dried in a sterilization bag at 40° C. for 5 hours to obtain a cell culture substrate 23.

Figure 7:
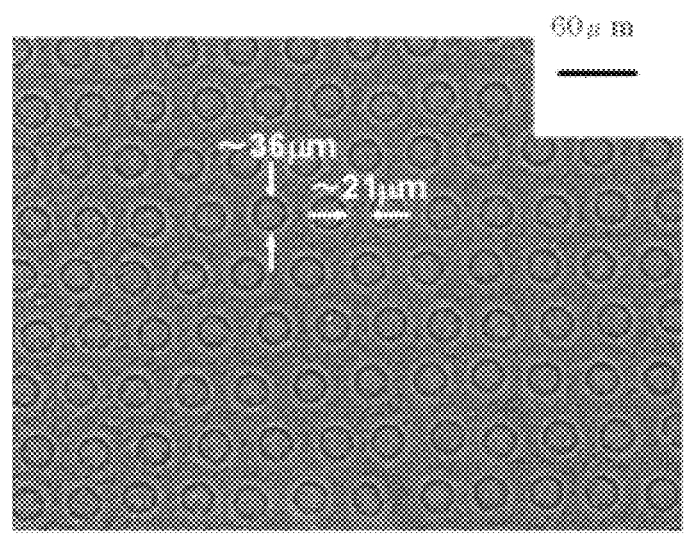
FIG. 7 is an optical micrograph of a cell culture substrate (Example 23) obtained by applying a dispersion (L2) in a circle pattern.

This cell culture substrate 23 was observed under an optical microscope. As a result, a pattern in which dots with a diameter of about 36 µm were formed on the one side of the polystyrene substrate was observed. The gap between adjacent dots was about 21 µm (FIG. 7).

[Culturing of Balb3T3 Cells (Mouse Tumor Fibroblast Cells)]

The cell culture substrate 23 thus obtained was placed in a 60 mm polystyrene schale (60 mm/non-treated dish, available from Asahi Techno Glass Corporation), a predetermined amount of Dulbecco's modified Eagle's medium (DMEM) with 10% FBS (available from Nissui Pharmaceutical Co., Ltd.) was added thereto, Balb3T3 cells were seeded (at a concentration of $1.0 \times 10^4$ cell/cm$^2$) and cultured in 5% carbon dioxide at 37° C. After being proliferated for 46 hours, the cells were observed under a microscope. The results indicated that the applied region was almost entirely covered with cells. Then, the 37° C. medium was replaced with a 4° C. medium, then allowed to stand for several minutes. As a result, it was observed that cells were detached from the cell culture substrate 23. A ratio of detached cell area and total area of the proliferated cells before detachment was calculated. Also, the time required for detachment was recorded (Table 1, cell detachment collection=98%, the time required for detachment=9 minutes).

Meanwhile, in the same manner, Balb3T3 cells were cultured using the polystyrene substrate. As a result, the Balb3T3 cells underwent almost no proliferation, indicating that this polystyrene substrate is not suitable for culturing the seeded cells.

It can be seen from Example 23 that, by applying the dispersion (L2) comprising a small amount of poly(N-isopropylacrylamide) in a dot pattern, similar to the cell culture substrate 20 whose entire surface was applied, the cells can be cultured throughout the applied region and unapplied region, and excellent cell detachability can be realized even when only a small amount of poly(N-isopropylacrylamide) is added.

Example 24

In this Example, a cell culture substrate was prepared by the third preparation method.
[Preparation of Reaction Solution Comprising Monomer (a), Inorganic Material (C) and Aqueous Medium (W)]
0.91 g of polyoxypropylene monoacrylate "Brenmer AP-400" (available from NOF Corporation) as a monomer (a), 0.4 g (solid content: 0.08 g) of Snotex 20 (20 wt % colloidal silica aqueous solution available from Nissan Chemical Industries, Ltd.) as a silica, 100 μl of 20 wt % sodium dodecylbenzene sulfonate (available from Wako Pure Chemical Industries, Ltd.) as a surfactant and 10 g of water as an aqueous medium (W) were uniformly mixed to prepare a reaction solution (F24).
[Preparation of Solution of Polymerization Initiator (D) in Solvent (E)]
The same solution (S1) as in Example 16 was used.
[Preparation of Dispersion (L) of Composite (X) (First Step)]
30 μl of the solution (S1) was added to the entire amount of the reaction solution (F24) and was uniformly dispersed. The dispersion was irradiated with ultraviolet rays (with intensity 40 mW/cm$^2$ at 365 nm) for 180 seconds to obtain a slightly milky white dispersion (L3) of composite (X).
In this reaction system, Ra was 0.09 and the concentration (wt %) of the inorganic material (C) was 0.79(%)<12.4Ra+ 0.05=1.17.
[Preparation of Cell Culture Substrate (Second Step)]
0.7 g of the poly(N-isopropylacrylamide) aqueous solution (5) of Example 20 was added to the entire amount of the dispersion (L3) and was uniformly mixed. The mixture was applied to a 60 mm polystyrene schale (60 mm/non-treated dish, available from Asahi Techno Glass Corporation), thinly applied to the schale surface at 2,000 rpm using a spin coater, and dried in a hot air drier at 80° C. for 10 min. Then, the schale was washed with sterile water and dried in a sterilization bag to obtain a cell culture substrate 24.
Adhesion of the dry film was tested in the same manner as in Example 16. As a result, the applied film was not detached and exhibited superior adhesion to the substrate.
[Culturing of Normal Human Dermal Fibroblast Cells]
Normal human dermal fibroblast cells were cultured using the cell culture substrate 24 in the same manner as in Example 16. Upon confirming sufficient proliferation of the cell, the medium (at 37° C.) was replaced with a 4° C. medium to naturally detach the proliferated cells. A ratio of detached cell area and total area of the proliferated cells before detachment was calculated (Table 1, cell detachment collection=95%, the time required for detachment=10 minutes).

Example 25

This Example illustrates performance of radiation-sterilized cell culture substrates.
[Radiation-Sterilization of Cell Culture Substrate]
The cell culture substrate 21 of Example 21 was irradiated with gamma rays such that an absorbed dose was adjusted to 10 kGy (irradiation was performed in Japan Irradiation Service Co., Ltd.).
For reference, irradiation with gamma rays was performed in the same manner as illustrated using a commercially available temperature-response cell culture substrate for cell sheet recovery, UpCell, (6 cm dish, available from CellSeed Inc.).

[Culturing of Normal Human Umbilical Venous Endothelial Cells]
A predetermined amount of Hu-media-EB2 medium comprising 10% FBS (available from Cell Systems Corporation) was added to the gamma rays-irradiated cell culture substrate 21 thus obtained, and normal human umbilical venous endothelial cells were seeded (at a concentration of 1.2×10$^4$ cell/cm$^2$) thereon and were cultured in 5% carbon dioxide at 37° C. Upon confirming sufficient proliferation of the cell, the medium (at 37° C.) was removed by aspiration and a 4° C. medium was added thereto, then allowed to stand for a pre-determined period to naturally detach the proliferated cells. A ratio of detached cell area and total area of the proliferated cells before detachment was calculated. Also, the time required for detachment was recorded (Table 1, cell detachment collection=96%, the time required for detachment=13 minutes).
Meanwhile, normal human umbilical venous endothelial cells were cultured in the same manner as illustrated above using the cell culture substrate 21 of Example 21 (without any irradiation) and then naturally detached. As a result, cell detachment collection was 95% and the time required for detachment was 14 minutes. Also, normal human umbilical venous endothelial cells were cultured in the same manner as illustrated above using gamma rays-irradiated commercially available UpCell and then naturally detached. As a result, cell detachment collection was 30% and the time required for detachment was 40 minutes.
Meanwhile, normal human umbilical venous endothelial cells were cultured in the same manner as illustrated above using non-irradiated commercially available UpCell and then naturally detached. As a result, cell detachment collection was 100% and the time required for detachment was 15 minutes.
It can be seen from Example 25 that radiation-sterilization of the cell culture substrate 21 did not affect culturing and detachment of cells. Meanwhile, commercially available UpCell exhibited considerably deteriorated cell detachment after radiation-sterilization.

Example 26

Cell Culture Substrate Comprising No Polymer (B)

[Preparation of Cell Culture Substrate]
The dispersion (L1) of Example 16 was placed in a polystyrene schale (60 mm/non-treated dish, available from Asahi Techno Glass Corporation), thinly applied to the schale surface at 2,000 rpm using a spin coater, and dried in a hot air drier at 80° C. for 10 min. Then, the schale was washed with sterile water and dried in a sterilization bag to obtain a cell culture substrate 26.
The adhesion of the dry film was tested in the same manner as in Example 16. As a result, it was confirmed that the applied film was not detached and exhibited superior adhesion to the substrate.
[Culturing of Normal Human Dermal Fibroblast Cells]
Normal human dermal fibroblast cells were cultured using the cell culture substrate 26 in the same manner as in Example 16. The medium (at 37° C.) was replaced with a 4° C. medium, thereby the proliferated cells were naturally detached and a ratio of detached cell area and total area of the proliferated cells before detachment was calculated (Table 1, cell detachment collection=10%, the time required for detachment=30 minutes). The cell proliferation of the cell culture substrate was almost identical to that of the cell culture substrate 1.

Comparative Example 7

This example illustrates a case where the concentration of the inorganic material (C) exceeds the range defined by Formula (3).
[Preparation of Reaction Solution Comprising Monomer (a), Water-Swellable Inorganic Material (C) and Aqueous Medium (W)]

1.32 g of 2-methoxyethyl acrylate (available from Toagosei Co., Ltd.) as a monomer (a), 0.25 g of water-swellable clay mineral Laponite XLG (available from Rockwood Additives Ltd.) as an inorganic material (C), 25 µl of the solution (S1) as a water-insoluble polymerization initiator (d1), and 10 g of water as an aqueous medium (W) were uniformly mixed to prepare a reaction solution (F7C).

The reaction solution (F7C) was irradiated with ultraviolet rays (with intensity 40 mW/cm$^2$ at 365 nm) for 180 seconds while being stirred with a magnetic stirrer. As a result, the reaction solution (F7C) was entirely gelled. The gel was not dissolved or dispersed and was maintained even when added to a large amount of water.

In this reaction system, Ra was 0.19 and the concentration (wt %) of the inorganic material (C) was 2.42%>0.87Ra+2.17=2.34.

It can be seen from this Comparative Example that when the concentration (wt %) of the inorganic material (C) exceeds the range defined by Formula (3), the reaction solution was entirely gelled, the dispersion (L) of composite (X) was not obtained, and preparation of cell culture substrates by coating the schales in accordance with first and third preparation methods cannot be thus realized.

Comparative Example 8

This Example illustrates preparation of cell culture substrates composed of hydrogel having a three-dimensional network structure composed of poly(N-isopropylacrylamide) and an inorganic material (C).
[Preparation of Reaction Solution Comprising Monomer, Inorganic Material (C) and Aqueous Medium (W)]

1.13 g of N-isopropylacrylamide (available from Kohjin Co., Ltd.) as a monomer, 0.4 g of Laponite XLG (available from Rockwood Additives Ltd.) as an inorganic material (C), and 10 g of water as an aqueous medium (W) were uniformly mixed to prepare a reaction solution (F8C).
[Preparation of Solution of Polymerization Initiator (d$_1$) in Solvent (E)]

98 g of polyoxypropylene monoacrylate "Brenmer AP-400" (available from NOF Corporation) as a solvent (E) and 2 g of 1-hydroxycyclohexyl phenyl ketone "Irgacure 184" (available from Ciba-Geigy Ltd.) as a polymerization initiator (d$_1$) were uniformly mixed to prepare a solution (S2).
[Preparation of Cell Culture Substrate Composed of Hydrogel]

50 µl of the solution (S2) was added to the entire amount of the reaction solution (F8C), uniformly dispersed using an ultrasonic homogenizer. The resulting dispersion was placed in a 60 mm polystyrene schale (60 mm/non-treated dish, available from Asahi Techno Glass Corporation) and thinly applied to the schale surface at 2,000 rpm using a spin coater, then N-isopropylacrylamide was polymerized by irradiation of ultraviolet rays (with intensity 40 mW/cm$^2$ at 365 nm) for 180 seconds, while cooling the schale with an ice, to form a hydrogel thin layer.

Then, the schale was washed with sterile water. As a result, the hydrogel thin layer was detached from the schale, and cell culture substrate which comprises hydrogel thin layer laminated on the schale was not obtained.

The hydrogel thin layer detached during washing was dried on the schale and was provided for cell culture.
[Culturing Normal Human Dermal Fibroblast Cells]

The dried hydrogel thin layer was placed in the schale, a predetermined amount of CS-C complete medium (available from Cell Systems Corporation) was added thereto, and normal human dermal fibroblast cells were seeded (at a concentration of 1.2×10$^4$ cell/cm$^2$) and cultured in 5% carbon dioxide at 37° C.

Upon confirming sufficient proliferation of the cells, the medium (at 37° C.) was replaced with a 4° C. medium, thereby the proliferated cells were naturally detached. A ratio of detached cell area and total area of the proliferated cells before detachment was calculated. Also, the time required for detachment was recorded (Table 1, cell detachment collection=70%, the time required for detachment=30 minutes).

It can be seen from this Comparative Example that the cell culture substrate comprising hydrogel having a three-dimensional network structure composed of the polymer (B) having a lower critical solution temperature and clay mineral exhibited weak adhesion to a support such as plastic and a support-integrated cell culture substrate cannot be thus prepared.

TABLE 1

| | Cell detachment collection (%) | The time required for detachment (min) | Reference |
|---|---|---|---|
| Ex. 16 | 93 | 18 | Cell F |
| Ex. 17 | 98 | 10 | Cell F |
| Ex. 18 | 100 | 12 | Cell F |
| Ex. 19 | 78 | 30 | Cell F |
| Ex. 20 | 100 | 7 | Cell F |
| Ex. 21 | 100 | 15 | Cell F |
| Ex. 22 | 79 | 29 | Cell F |
| Ex. 23 | 98 | 9 | Cell T |
| Ex. 24 | 95 | 10 | Cell F |
| Ex. 25 | 96 | 13 | Cell H |
| Ex. 26 | 10 | 30 | Comprising no polymer (B), Cell F |
| Comp. Ex. 7 | — | — | Impossible manufacturing of culture substrate |
| Comp. Ex. 8 | 70 | 30 | Only hydrogel thin film (Not adhered to support) |

Note:
(1) Cell F: normal human dermal fibroblast cells
(2) Cell T: mouse tumor fibroblast cell (Balb3T3)
(3) Cell H: normal human umbilical venous endothelial cells As can be seen from Examples and Comparative Examples, the cell culture substrate of the present invention exhibited good adhesion to a support composed of a different material and excellent cell culturing and detachment properties.

Also, the cell culture substrate can be readily prepared in an extremely short time without any need to avoid oxygen.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. An organic-inorganic composite dispersion comprising particles of a composite (X) dispersed in an aqueous medium (W), the composite (X) having a three-dimensional network formed of a polymer (A) of a monomer comprising a monomer (a) represented by Formula (1)

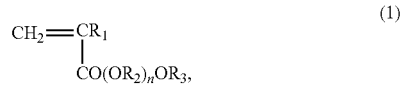

where $R_1$ is a hydrogen atom or a methyl group, $R_2$ is a $C_2$-$C_3$ alkylene group, $R_3$ is a $C_1$-$C_2$ alkyl group and n is an integer of 1 to 9,
and at least one inorganic material (C) selected from a water-swellable clay mineral and silica, wherein the particles of the composite (X) have a structure in which the inorganic material (C) is uniformly dispersed in the polymer (A), the concentration (wt %) of the inorganic material (C) in the aqueous medium (W) is
 <12.4Ra+0.05 when Ra<0.19, or
 <0.87Ra+2.17 when Ra>0.19, and
Ra is from 0.01 to 10,
 where the concentration (wt %) of the inorganic material (C) is a value calculated by dividing the weight of the inorganic material (C) by the total weight of the aqueous medium (W) and the inorganic material (C) and multiplying the resulting value by 100, and
 Ra is a weight ratio ((C)/(A)) of the inorganic material (C) to the polymer (A).

2. An organic-inorganic composite dispersion comprising particles of a composite (X) dispersed in an aqueous medium (W), the composite (X) having a three-dimensional network formed of a polymer (A) of a monomer comprising a monomer (a) represented by Formula (1)

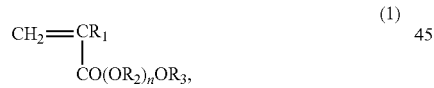

where $R_1$ is a hydrogen atom or a methyl group, $R_2$ is a $C_2$-$C_3$ alkylene group, $R_3$ is a $C_1$-$C_2$ alkyl group and n is an integer of 1 to 9,
and at least one inorganic material (C) selected from a water-swellable clay mineral and silica, wherein the particles of the composite (X) have a core-shell structure comprising a core portion in which the inorganic material (C) is dispersed in the polymer (A), and a shell portion, wherein dispersion density of the inorganic material (C) in the shell portion is higher than in the core portion,
wherein Ra is from 0.01 to 10, where Ra is a weight ratio ((C)/(A)) of the inorganic material (C) to the polymer (A).

3. A dry film of the composite (X) obtained by drying the organic-inorganic composite dispersion according to claim 1.

4. A laminate having a laminate structure comprising a support and the dry film according to claim 3 formed on the support.

5. A cell culture substrate having the laminate structure according to claim 4.

6. An antifogging material having the laminate structure according to claim 4.

7. A method for preparing an organic-inorganic composite dispersion according to claim 1,
 the method comprising:
 dissolving or uniformly dispersing the monomer (a), the inorganic material (C), and a polymerization initiator (D) in the aqueous medium (W) and polymerizing the monomer (a) to form the particles of the composite (X).

8. A cell culture substrate comprising: a composite (X) obtained from the organic-inorganic composite dispersion of claim 1; and
 a polymer (B) having a lower critical solution temperature, wherein the content of the polymer (B) with respect to the total weight of the cell culture substrate is 0.0001% to 40% by weight.

9. The cell culture substrate according to claim 8, wherein the polymer (B) is exposed at a cell culture surface of the cell culture substrate.

10. The cell culture substrate according to claim 8, wherein the polymer (B) is a polymer of at least one monomer (b) selected from the group consisting of N-substituted (meth)acrylamide derivatives and N,N-di-substituted (meth)acrylamide derivatives.

11. The cell culture substrate according to claim 10, wherein the monomer (b) is at least one selected from the group consisting of N-isopropyl (meth)acrylamide, N-n-propyl (meth)acrylamide, N-cyclopropyl (meth)acrylamide, N-ethoxyethyl (meth)acrylamide, N-tetrahydrofurfuryl (meth)acrylamide, N-ethyl acrylamide, N-ethyl-N-methyl acrylamide, N,N-diethyl acrylamide, N-methyl-N-n-propyl acrylamide, N-methyl-N-isopropyl acrylamide, N-acryloyl piperidine and N-acryloyl pyrrolidine.

12. A method for preparing a cell culture substrate comprising: a composite (X) obtained from the organic-inorganic composite dispersion of claim 1; and
 a polymer (B) having a lower critical solution temperature, the method comprising:
 a first step of mixing the monomer (a), the inorganic material (C) and a polymerization initiator (D) in an aqueous medium (W) such that the concentration of the inorganic material (C) in the aqueous medium (W) is within the range represented by the following Formula (2) or (3), and polymerizing the monomer (a) to provide a dispersion (L) of the composite (X) comprising the polymer (A) and the inorganic material (C);
 a second step of applying the dispersion (L) to a support and drying the support to form a thin layer of the composite (X);
 a third step of applying a solution of a water-insoluble polymerization initiator (D) in a solvent (E) to a surface (S) of the thin layer of the composite (X) and volatilizing the solvent (E); and
 a fourth step of applying an aqueous solution of a monomer (b) undergoing polymerization to form the polymer (B) to the surface (S) and polymerizing the monomer (b) by UV irradiation.

13. A method for preparing a cell culture substrate comprising: a composite (X) obtained from the organic-inorganic composite dispersion of claim 1; and
 a polymer (B) having a lower critical solution temperature, the method comprising:
 a first step of mixing the monomer (a), the inorganic material (C) and a polymerization initiator (D) in an aqueous medium (W) such that the concentration of the inorganic material (C) in the aqueous medium (W) is within the range represented by the following Formula (2) or (3), and polymerizing the monomer (a) to provide a dispersion (L) of the composite (X) comprising the polymer (A) and the inorganic material (C); and a second step of adding the polymer (B) to the dispersion (L), mixing the ingredients, applying the resulting mixture to a support and drying the support.

14. A dry film of the composite (X) obtained by drying the organic-inorganic composite dispersion according to claim 2.

15. The composite dispersion according to claim 1, wherein the particles of the composite have a particle size of 50 nm to 5 μm.

16. The composite dispersion according to claim 2, wherein the particles of the composite have a particle size of 50 nm to 5 μm.

17. The composite dispersion according to claim 2, wherein the concentration (wt %) of the inorganic material (C) in the aqueous medium (W) is <12.4Ra+0.05 when Ra<0.19, or <0.87Ra+2.17 when Ra≧0.19, where the concentration (wt %) of the inorganic material (C) is a value calculated by dividing the weight of the inorganic material (C) by the total weight of the aqueous medium (W) and the inorganic material (C) and multiplying the resulting value by 100.

18. A laminate having a laminate structure comprising a support and the dry film according to claim 14 formed on the support.

19. A cell culture substrate having the laminate structure according to claim 18.

20. An antifogging material having the laminate structure according to claim 18.

21. A method for preparing an organic-inorganic composite dispersion according to claim 17, the method comprising:

dissolving or uniformly dispersing the monomer (a), the inorganic material (C), and a polymerization initiator (D) in the aqueous medium (W) and polymerizing the monomer (a) to form the particles of the composite (X).

22. A cell culture substrate comprising a composite (X) obtained from the organic-inorganic composite dispersion of claim 2, and a polymer (B) having a lower critical solution temperature, wherein the content of the polymer (B) with respect to the total weight of the cell culture substrate is 0.0001% to 40% by weight.

23. A method for preparing a cell culture substrate comprising a composite (X) obtained from the organic-inorganic composite dispersion of claim 17, and a polymer (B) having a lower critical solution temperature, the method comprising:

a first step of mixing the monomer (a), the inorganic material (C) and a polymerization initiator (D) in an aqueous medium (W) such that the concentration of the inorganic material (C) in the aqueous medium (W) is within the range represented by the following Formula (2) or (3), and polymerizing the monomer (a) to provide a dispersion (L) of the composite (X) comprising the polymer (A) and the inorganic material (C);

a second step of applying the dispersion (L) to a support and drying the support to form a thin layer of the composite (X);

a third step of applying a solution of a water-insoluble polymerization initiator (D) in a solvent (E) to a surface (S) of the thin layer of the composite (X) and volatilizing the solvent (E); and a fourth step of applying an aqueous solution of a monomer (b) undergoing polymerization to form the polymer (B) to the surface (S) and polymerizing the monomer (b) by UV irradiation.

24. A method for preparing a cell culture substrate comprising a composite (X) obtained from the organic-inorganic composite dispersion of claim 17, and a polymer (B) having a lower critical solution temperature, the method comprising:

a first step of mixing the monomer (a), the inorganic material (C) and a polymerization initiator (D) in an aqueous medium (W) such that the concentration of the inorganic material (C) in the aqueous medium (W) is within the range represented by the following Formula (2) or (3), and polymerizing the monomer (a) to provide a dispersion (L) of the composite (X) comprising the polymer (A) and the inorganic material (C); and a second step of adding the polymer (B) to the dispersion (L), mixing the ingredients, applying the resulting mixture to a support and drying the support.

* * * * *